US012751882B2

(12) United States Patent
Becker et al.

(10) Patent No.: US 12,751,882 B2
(45) Date of Patent: Oct. 6, 2026

(54) METHODS AND SYSTEMS FOR PROVIDING OPEN ACCESS POINT INDICATORS IN AN INFANT CARE STATION

(71) Applicant: GE Precision Healthcare LLC, Wauwatosa, WI (US)

(72) Inventors: Karen P. Becker, Phoenix, MD (US); Rajendra Naik, Bangalore (IN); Thomas L. Valent, Burlington, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 1137 days.

(21) Appl. No.: 17/836,718

(22) Filed: Jun. 9, 2022

(65) Prior Publication Data

US 2023/0181402 A1 Jun. 15, 2023

Related U.S. Application Data

(63) Continuation-in-part of application No. 17/550,809, filed on Dec. 14, 2021, now Pat. No. 12,414,890.

(51) Int. Cl.
*A61G 11/00* (2006.01)
*G16H 40/67* (2018.01)

(52) U.S. Cl.
CPC ............ *A61G 11/00* (2013.01); *G16H 40/67* (2018.01); *A61G 2203/46* (2013.01); *A61G 2203/70* (2013.01); *A61G 2205/20* (2013.01)

(58) Field of Classification Search
None
See application file for complete search history.

(56) References Cited

U.S. PATENT DOCUMENTS

| | | | | |
|---|---|---|---|---|
| 11,166,677 B2* | 11/2021 | Davis | ................... | A61B 5/0816 |
| 2002/0147381 A1* | 10/2002 | Kolarovic | .............. | A61G 11/00 318/471 |
| 2015/0182722 A1* | 7/2015 | Lesch | .................... | A61G 10/02 600/22 |
| 2022/0054342 A1* | 2/2022 | Kavoori Sethumadhavan | ............ | F21V 23/04 |

FOREIGN PATENT DOCUMENTS

| | | | | |
|---|---|---|---|---|
| BR | 102019023077 A2 * | 5/2021 | ............. | A61G 11/00 |
| CN | 103197532 A * | 7/2013 | | |
| CN | 110090123 A | 8/2019 | | |
| CN | 110368237 A | 10/2019 | | |

(Continued)

OTHER PUBLICATIONS

EP application 23175033.2 filed May 24, 2023—extended Search Report issued Oct. 23, 20223; 8 pages.

(Continued)

*Primary Examiner* — Charles A Marmor, II
*Assistant Examiner* — Marc D. Honrath

(57) ABSTRACT

An infant care station can include a lighting system, at least one access point, and a processor that can detect that the at least one access point is open. The processor can also provide, using the lighting system, a first color light in response to the detecting that the at least one access point is open, and provide the first color light with a modified brightness or provide a second color light with the lighting system after a predetermined period of time elapses with the at least one access point being open.

6 Claims, 13 Drawing Sheets

(56) References Cited

FOREIGN PATENT DOCUMENTS

| | | | | | |
|---|---|---|---|---|---|
| CN | 111857210 A | * | 10/2020 | ............. | G05D 27/02 |
| CN | 113749885 A | | 12/2021 | | |
| CN | 114442500 A | * | 5/2022 | ........... | G05B 19/418 |

OTHER PUBLICATIONS

CN110090123—English abstract; Espacenet search results Aug. 1, 2023; 1 page.
CN110368237—English abstract; Espacenet search results Aug. 1, 2023; 1 page.
CN113749885—English Abstract; Espacenet search results Aug. 1, 2023; 1 page.
EP application 22210113.1 filed Nov. 29, 2022—extended Search Report issued May 8, 2023; 40 pages.

* cited by examiner

100

300

400

700

800

900A

900B

1300

1400

METHODS AND SYSTEMS FOR PROVIDING OPEN ACCESS POINT INDICATORS IN AN INFANT CARE STATION

CROSS-REFERENCE TO RELATED APPLICATIONS

The present matter is a continuation-in-part of and claims priority to U.S. patent application Ser. No. 17/550,809, filed Dec. 14, 2021, the contents of which are incorporated herein by reference.

BACKGROUND

The present disclosure generally relates to infant care stations, and more specifically to providing open access point indicators for an enclosure of an infant care station.

Some neonates are not physiologically well enough developed to be able to survive without special medical attention. A frequently used medical aid for such infants is the incubator. One objective of the incubator is to provide an environment which will maintain the neonate at a minimum metabolic state thereby permitting as rapid physiological stability as possible. Neonatal incubators create a microenvironment that is thermally neutral where a neonate can minimize energy expenditure. These incubators typically include a humidifier and a heater and associated control system that controls the humidity and temperature in the neonatal microenvironment. The humidifier comprises a device that evaporates an evaporant, such as distilled water, to increase relative humidity of air within the neonatal microenvironment. The humidifier is typically controllable such that the amount of water, or water vapor, added to the microenvironment is adjustable in order to control the humidity to a desired value. The heater may be, for example, an air heater controllable to maintain the microenvironment area to a certain temperature. Radiant warmers may be used instead of incubators for some neonates where open patient access is useful. In still other embodiments, hybrid incubator/radiant warming systems may be utilized.

Since the microenvironment is accurately controlled in a neonatal care system, the care system includes an enclosure that is sealed as much as possible to help maintain the controlled microenvironment. Such an enclosure will typically include four sidewalls or side panels and a top hood that surround an infant support platform. Typically, one or more of the side panels can include access points, such as porthole doors, and a removable top, among others, that enable clinicians to access neonates in the microenvironment. In some examples, the access points may not be fully closed or sealed, which can alter the conditions of the microenvironment.

BRIEF DESCRIPTION

This Brief Description is provided to introduce a selection of concepts that are further described below in the Detailed Description. This Summary is not intended to identify key or essential features of the claimed subject matter, nor is it intended to be used as an aid in limiting the scope of the claimed subject matter.

An infant care station can include sensors to detect an environmental characteristic of the infant care station, an access point to access a microenvironment of the infant care station, and a processor to obtain a sealed measurement for the infant care station with the access point in a sealed position. The processor can also obtain the environmental characteristic from sensors monitoring the microenvironment of the infant care station. Additionally, the processor can determine a difference between the environmental characteristic and the sealed measurement and generate an alert indicating an access point sealing issue based on the difference exceeding a predetermined threshold. The access point sealing issue, as referred to herein, can indicate an unexpected open or unsealed access point, or an unexpected, sealed access point.

In some examples, the access point can include a canopy, a porthole door, equipment access point, or a combination thereof. In one aspect, the processor can transmit the alert to an external computing device or a remote display device. In some examples, the processor can display the alert in a user interface coupled to the system.

In one aspect, the environmental characteristic can include a pressure value, a humidity value, an oxygen value, a temperature control loop value, or a combination thereof. In some examples, the sensors can include a pressure sensor, an oxygen sensor, a humidity sensor, or a combination thereof.

In one aspect, the sensors are coupled to an enclosure of the system, wherein the enclosure supports the microenvironment. In some examples, the alert can include an audio feedback, haptic feedback, or visual feedback representing a message that the at least one access point is unsealed. In some examples, the infant care station can include an ambient sensor, wherein the ambient sensor can detect an ambient measurement, and wherein the processor can generate a second alert in response to detecting a difference between the ambient measurement and the environmental characteristic that exceeds an ambient threshold. In some examples, the sensors can include a pressure sensor within the microenvironment and the environmental characteristic can include a pressure value obtained from the microenvironment by the pressure sensor.

In some examples, a method can include obtaining an ambient air measurement from one or more ambient air sensors for an environment proximate to an infant care station. The method can also include obtaining an environmental characteristic from one or more microenvironment sensors and determining a difference between the environmental characteristic and the ambient measurement exceeds a predetermined threshold. Additionally, the method can include generating an alert indicating an access point sealing issue in the infant care station based on the difference exceeding the predetermined threshold. In one aspect, the method can include preventing the alert from being generated in response to detecting a user in proximity sensor data within a predetermined distance from the infant care station.

In one aspect, a non-transitory machine-readable medium for detecting an access point sealing issue in an infant care station can include a plurality of instructions that cause a processor to obtain a sealed measurement for the infant care station with the at least one access point in a sealed position, wherein the at least one access point comprises a canopy, a porthole door, an equipment access point, or a combination thereof. The plurality of instructions can also cause the processor to obtain an environmental characteristic from the one or more sensors and determine a difference between the environmental characteristic and the sealed measurement exceeds a predetermined threshold. In some examples, the plurality of instructions can also cause the processor to generate an alert indicating an access point sealing issue in the infant care station based on the difference exceeding the predetermined threshold.

In some examples, an infant care station can include a lighting system, at least one access point, and a processor that can detect that the at least one access point is open. The processor can also provide, using the lighting system, a first color light in response to the detecting that the at least one access point is open, and provide the first color light with a modified brightness or provide a second color light with the lighting system after a predetermined period of time elapses with the at least one access point being open.

In one aspect, a method for illuminating an infant care station can include detecting that at least one access point is open using a sensor in the infant care station, providing, using a lighting system, a first color light in response to the detecting that the at least one access point is open, and providing the first color light with a modified brightness or provide a second color light with the lighting system after a predetermined period of time elapses with the at least one access point being open.

In another aspect, a non-transitory machine-executable media can include a plurality of instructions that in response to execution by a processor, cause the processor to detect that the at least one access point is open. The plurality of instructions can also cause the processor to provide, using the lighting system, a first color light in response to the detecting that the at least one access point is open and provide the first color light with a modified brightness or provide a second color light with the lighting system after a predetermined period of time elapses with the at least one access point being open. In some examples, the plurality of instructions can cause the processor to obtain lighting system data representing the first color, the second color, and a time that the access point is open and transmit the lighting system data to a remote device.

Various other features, objects, and advantages of the invention will be made apparent from the following description taken together with the drawings.

BRIEF DESCRIPTION OF THE DRAWINGS

The drawings illustrate the best mode presently contemplated of carrying out the disclosure. In the drawings.

Figure 1:
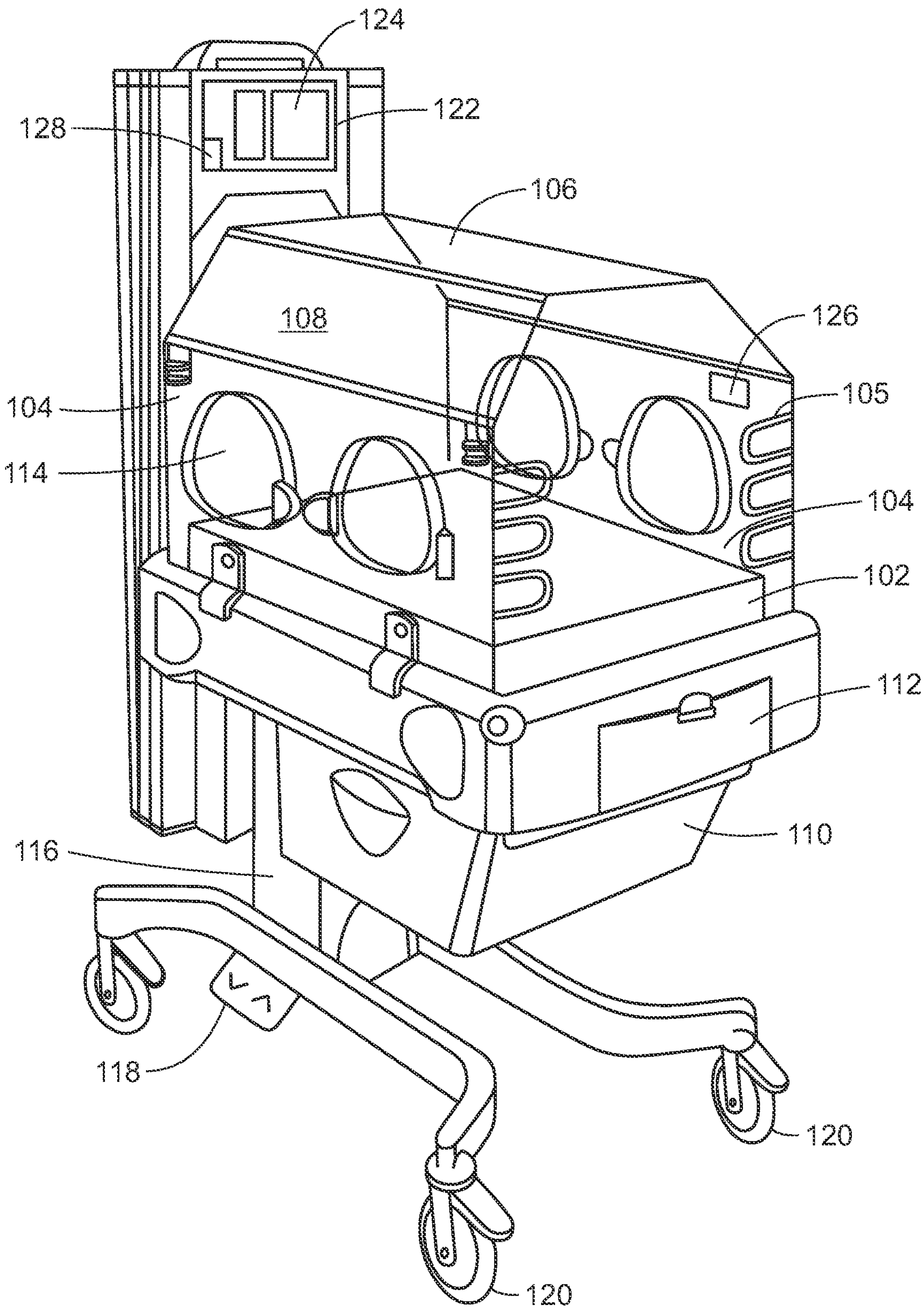
FIG. 1 is a perspective view of an example infant care station in accordance with one example.

The drawings illustrate specific aspects of the described components, systems and methods for providing a neonatal incubator system. Together with the following description, the drawings demonstrate and explain the principles of the structures, methods, and principles described herein. In the drawings, the thickness and size of components may be exaggerated or otherwise modified for clarity. Well-known structures, materials, or operations are not shown or described in detail to avoid obscuring aspects of the described components, systems and methods.

DETAILED DESCRIPTION

Embodiments of the present disclosure will now be described, by way of example, with reference to FIGS. 1-14. Infant care stations can provide microenvironments for infant patients receiving medical care. Infant care stations, as referred to herein, can include incubators, warmers, or devices that support one or more features of incubators and warmers. In some examples, the infant care stations can enable clinicians to access the patient by opening one or more access points. An access point, as referred to herein, includes porthole doors that reside within one or more walls of the infant care stations, removable canopies of infant care stations, equipment access points, and the like. For example, a clinician may disengage any suitable latch coupled to the porthole doors to open the porthole doors and access a patient residing within an infant care station. However, porthole doors can be accidentally left open, which can result in unexpected conditions within the microenvironment of the infant care station. Also, radiant heaters of an infant care station can be improperly engaged when an infant care station transitions from a warmer with an open top or canopy to an incubator with a closed canopy. When the radiant heater remains engaged for an extended period of time with the canopy of the infant care station in a closed position, unexpected conditions can arise in the microenvironment.

Techniques described herein enable an infant care station to detect when an access point is sealed or unsealed. In some examples, an infant care station can include one or more sensors (also referred to herein as microenvironment sensors) that can measure, obtain, or otherwise detect an environmental characteristic of the microenvironment. The environmental characteristic, as referred to herein, can include a pressure level, an oxygen level, a humidity level, or a combination thereof obtained from the microenvironment of the infant care station. In some examples, the infant care station can monitor the environmental characteristic and determine when an access point is left unsealed or open based on a previously obtained sealed measurement from the microenvironment of the infant care station. The sealed measurement, as referred to herein, can indicate an expected pressure, oxygen level, humidity level, and the like, within the microenvironment when the porthole doors are in a sealed or closed position. Alternatively, the infant care station can detect an ambient characteristic or measurement, such as a pressure, oxygen level, or humidity level, from the surrounding environment outside of the infant care station. In some examples, the infant care station can compare the ambient characteristic to the environmental characteristic to determine if an access point is sealed or unsealed. In some examples, a sealed or unsealed access point refers to a gap between an access point and an infant care station exceeding a predetermined threshold. For example, a sealed access point can refer to a canopy or a porthole door, among other access points, that is positioned proximate walls of an infant care station such that a gap exists between the walls and the canopy or porthole door. In some examples, a gap that is smaller than a predetermined threshold represents a sealed access point and a gap greater than a predetermined threshold represents an unsealed access point.

An advantage that may be realized by the sealed access point illumination feature in the practice of some examples of the described systems and techniques is an additional safety mechanism to prevent an access point from remaining disengaged in an unsealed or open position for an extended period of time. The techniques herein can also prevent unexpected conditions within the microenvironment by detecting when an infant care station has transitioned from a warmer to an incubator and determining if a heater has turned off following the transition. Accordingly, techniques herein can prevent an unexpected alteration of the temperature, humidity, oxygen level, and the like, within the microenvironment of an infant care station. Techniques for illuminating sealed or unsealed access points are described in greater detail below in relation to FIGS. 1-14.

FIG. 1 is a perspective view of an example infant care station in accordance with one example. In the example of FIG. 1, an infant care station is depicted in which the infant care station is an incubator 100. The incubator 100 includes a horizontal surface 102 that is configured to support an infant patient (not depicted). It is to be understood that the incubator 100 may have the ability or control to move, rotate, or incline the horizontal surface 102; however, it will be understood that the horizontal surface 102 will generally remain horizontal such as to minimize movement of the infant patient within the incubator 100 due to gravity.

One or more walls 104 extend generally vertically from the horizontal surface 102. In the embodiment depicted in FIG. 1 of the incubator 100, four walls extend vertically from the horizontal surface 102 to define the rectangular shape of the incubator 100. However, it will be understood that in alternative examples, various numbers of walls 104 may be used to define the incubator into various geometric shapes which may include, but are not limited to, circles or hexagons. The incubator 100 can further include a canopy 106 that extends over the horizontal surface 102. In some examples, the canopy 106 can include multiple components or surfaces, or the canopy may be curved or domed in shape.

While the incubator of FIG. 1 is depicted with the horizontal surface 102, walls 104, and canopy 106 being connected, it will be understood that in alternative examples, including those described in greater detail herein, the horizontal surface 102, walls 104, and canopy 106 may be individual components that also may be movable with respect to each other. For example, the canopy 106 can transition from a closed position to an open position in which any suitable portion of the canopy 106 is raised away from the walls 104 to allow the microenvironment to be exposed to the surrounding environment of the incubator 100.

The horizontal surface 102, walls 104, and canopy 106 can define a microenvironment 108 contained within these structures. In some examples, the incubator 100 is configured such that the microenvironment 108 surrounds the infant patient (not depicted) such that the infant patient is only exposed to a controlled combination of environmental characteristics or conditions (temperature, humidity, $O_2$ concentration, etc.) selected by a clinician to promote the health and wellbeing of the infant patient. In some examples, the walls 104 further include portholes 114 that permit a clinician access into the microenvironment 108. The walls 104 can also include any number of equipment access points 105. The equipment access points 105 can include grommet seals (or any other suitable seals) for cables, harnesses, and other medical equipment access holes. In some examples, seals and other equipment can fall out from the equipment access points 105 or the seals and other equipment can be damaged when equipment hoses or cables are removed.

In some examples, the incubator 100 includes a base 110 that houses a convective heater 112. The convective heater 112 is operated such that air is drawn into the incubator 100, at which point the air may be filtered or sterilized in another manner, including the use of UV light before being passed by heating coils (not depicted) to heat the air to a target or set point temperature. The sterilized and heated air is blown into the microenvironment 108 through vents (not depicted) which are arranged along the walls 104. As is also known, the air may be entrained with supplemental gasses such as oxygen or may have added humidity such as to control these conditions within the microenvironment 108.

Examples of the incubator 100 further include a pedestal 116 connected to the base 110. The pedestal 116 includes mechanical components (not depicted), which may include, but are not limited to, servo motors, rack and pinion systems, or screw gear mechanisms that are operable by foot pedals 118 to raise or lower the base 110, effectively raising or lowering the position of the infant patient (not depicted) in relation to the clinician. The incubator 100 may be movable by wheels or casters 120 connected to the pedestal 116.

The example of the incubator 100 depicted in FIG. 1 includes a graphical display 122 that is mounted to a wall, the base 110, or the canopy 106 of the incubator 100 at a position external to the microenvironment 108. The graphical display 122 is operated by a processor to present a graphical user interface (GUI) 124. In the example illustrated, the graphical display 122 is a touch-sensitive graphical display and the GUI 124 is configured to specifically respond to inputs made by a clinician received through the touch-sensitive graphical display. During normal operation, the touch-sensitive graphical display 122 and touch-sensitive configured GUI 124 are used to control various functions of the incubator 100. The GUI 124 presents a variety of information, such as the air temperature and alarm indications. In some examples, the alarm indications can provide a message indicating an access point is unsealed or open, a change in environment characteristics, or a warning that a heater is still operational after the canopy 106 has been closed, among others.

In some examples, the walls 104 of the incubator 100 can be opened or closed to enable a clinician to access a patient residing in the incubator 100. For example, the walls 104 can serve as doors that open and close to either remove a patient from the incubator 100 or to place a patient into the incubator 100. As described in greater detail below in relation to FIGS. 2-6, the walls 104 can include any number of access points, such as portholes 114 covered by porthole doors, that enable access to a patient residing in a microenvironment of the incubator 100.

In some examples, the incubator 100 can include any number of sensors as part of a sensor system 126. The sensor system 126 can include pressure sensors, oxygen sensors, humidity sensors, and the like. In some examples, the sensor system 126 is connected to a host device 128 that controls the GUI 124. The sensor system 126 can transmit sensor data to the host device 128 and the host device 128 can determine if any access points, such as the canopy 106 or portholes 114, of the incubator 100 are unsealed or open. In some examples, the sensor system 126 can transmit sensor data indicating environmental characteristics of a microenvironment to a host device 128 using any suitable wired or wireless transmission protocol. The host device 128 can determine if the access points are unsealed or open based on generating a difference using the sensor data in real-time and sealed measurements previously obtained from the incubator 100 or an ambient sensor measurement as discussed in greater detail below in relation to FIG. 3.

Figure 2:
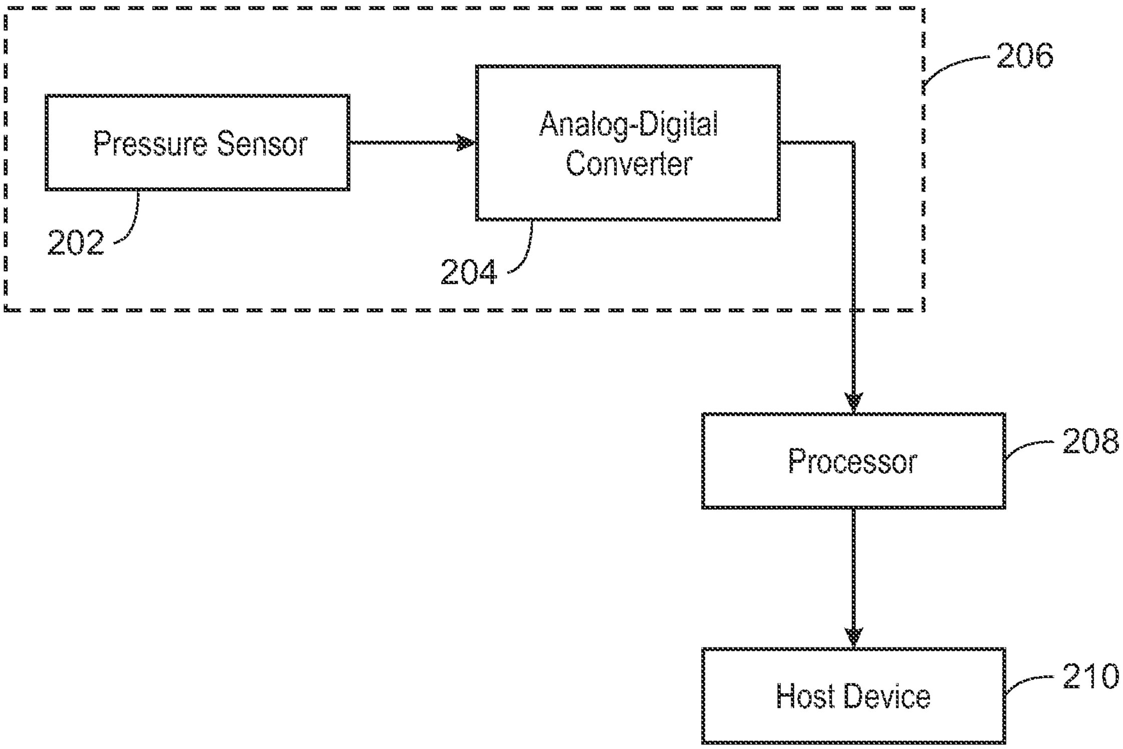
FIG. 2. is a block diagram of an example of a pressure sensor system within an infant care station.

FIG. 2. is a block diagram of an example of a pressure sensor system within an infant care station. In some examples, the pressure sensor 202 of an infant care station is used to determine an environmental characteristic of a microenvironment of an infant care station. The pressure sensor 202 can be coupled to an analog-to-digital converter 204, or the pressure sensor 202 and the analog-to-digital converter 204 can be combined to form an integrated pressure sensor 206. The analog-to-digital converter 204 or the integrated pressure sensor 206 can transmit sensor data to a processor 208 at any suitable time interval such as one second, 10 seconds, one minute, or the like. The processor 208 can transmit the sensor data to a host device 210, or the host device 128 of FIG. 1, among others. In some examples, either the processor 208 or the host device 210 can determine if an access point is open or unsealed by determining if a measurement from the microenvironment of an infant care station exceeds a predetermined difference with an ambient sensor value or a sealed measurement previously obtained within the infant care station. In some examples, the processor 208 can transmit sensor data or data calculated based on the sensor data to the host device 210 using any suitable wired or wireless protocol.

In some examples, an infant care station, such as the incubator 100 of FIG. 1, can include any number of pressure sensors 202, among other sensors. The host device 210 can obtain sensor data from the pressure sensors 202 and any other sensors and determine if an infant care station has one or more access points that are either in an open or closed position. Additionally, in some examples, the analog-to-digital converter 204 or the integrated pressure sensor 206 can include logic to pre-process the sensor data to detect incorrect sensor data and the like.

Figure 3:
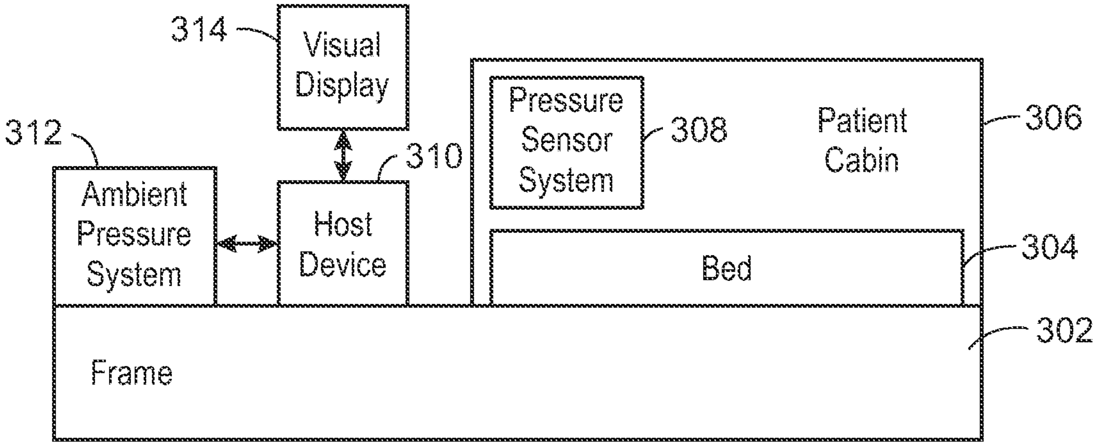
FIG. 3 depicts a block diagram of an example system for detecting an access point sealing issue in an infant care station.

FIG. 3 depicts a block diagram of an example system for detecting an access point sealing issue in an infant care station. In some examples, the infant care station 300 can include a frame 302 that supports a bed 304 within a patient cabin 306. The patient cabin 306 can include four or more walls and a canopy, among other components that enable a microenvironment to form within the patient cabin 306. For example, the patient cabin 306 can maintain a constant humidity, oxygen level, temperature, and the like for a patient residing on the bed 304. In some examples, a pressure sensor system 308 is coupled to the patient cabin such that the pressure sensor system 308 can determine a pressure of the microenvironment.

In some examples, the pressure sensor system 308 can periodically or continuously transmit pressure sensor data to a host device 310. The host device 310 can also obtain ambient sensor data or ambient measurements from ambient pressure sensors or an ambient pressure system 312 proximate to the host device 310. The ambient pressure system 312 can provide the pressure values from the environment outside of the microenvironment. In some examples, the pressure values obtained, detected, or otherwise received from the ambient pressure system 312 can indicate an altitude of an infant care station 300. For example, a lower pressure level can indicate that the infant care station 300 resides at a higher altitude.

In some examples, the host device 310 can obtain an environmental characteristic, such as a pressure of the microenvironment, from the pressure sensor system 308 and determine whether a difference between the environmental characteristic and the ambient measurement exceeds a predetermined threshold. If the difference does not exceed the predetermined threshold, the host device 310 may continue to monitor the microenvironment without generating an alert. If the difference does exceed the predetermined threshold, the host device 310 can generate an alert indicating an unsealed access point in the infant care station based on the difference exceeding the predetermined threshold.

In some examples, the alert can be provided to a user with the visual display 314, using haptic feedback, or audio feedback, among others. In some examples, the visual display 314 can be coupled to the host device 310 or the visual display 314 can reside in a remote location. The alert can include a message that the at least one access point is unsealed or that a canopy of an infant care station 300 has transitioned to a closed position from an open position.

In some examples, the host device 310 can obtain environmental characteristics from any number of sensors coupled to the infant care station 300. The sensors can monitor the oxygen level, humidity level, and the like, from within the microenvironment, or the sensors can monitor components that control the temperature of the microenvironment. For example, the host device 310 can detect a decrease in oxygen level of a microenvironment of an infant care station 300, which indicates an open access point, such as a porthole door or a canopy. The host device 310 can also detect an increase or decrease in power consumption by a convective heater, convective heater fan, among other heater components, of an infant care station 300.

It is to be understood that the block diagram of FIG. 3 is not intended to indicate that the infant care station 300 is to include all of the components shown in FIG. 3. Rather, the infant care station 300 can include fewer or additional components not illustrated in FIG. 3 (e.g., additional memory components, embedded controllers, additional modules, additional network interfaces, additional sensor devices, etc.).

Figure 4:
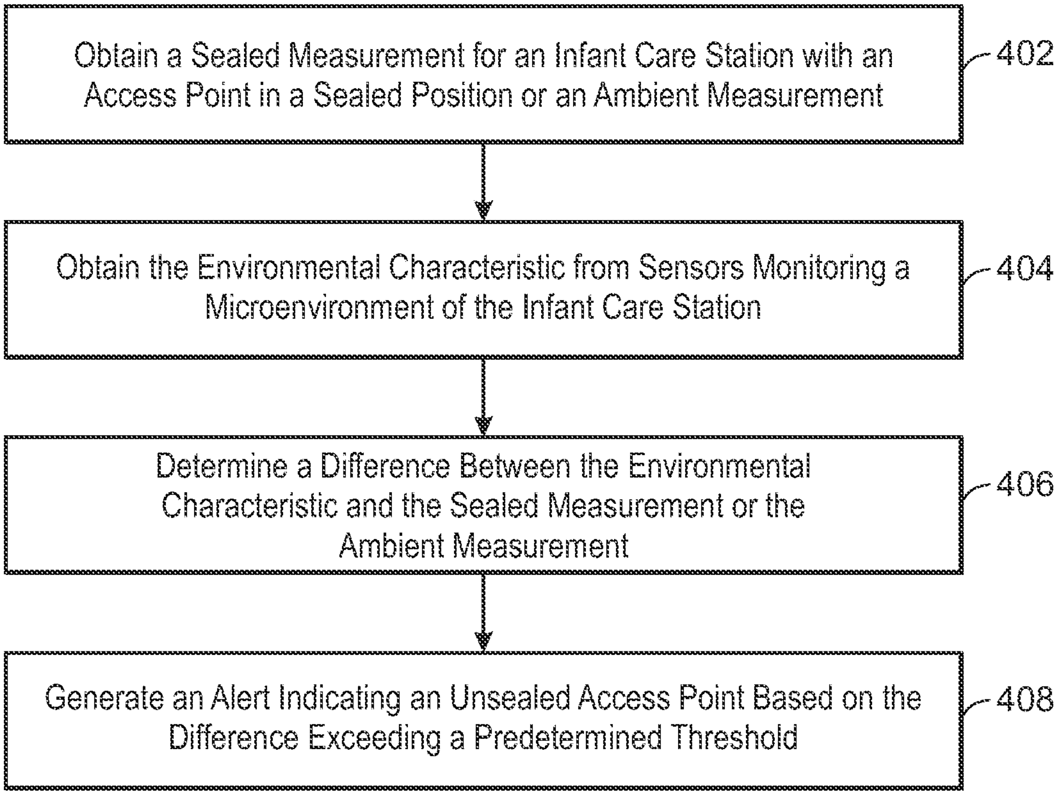
FIG. 4 depicts a process flow diagram of an example method for detecting an access point sealing issue in an infant care station.

FIG. 4 depicts a process flow diagram of an example method for detecting an access point sealing issue in an infant care station. The method 400 can be implemented with any suitable infant care station, such as the incubator 100 of FIG. 1 or the infant care station 300 of FIG. 3, among others.

At block 402, the method 400 can include obtaining, detecting, or otherwise receiving a sealed measurement for an infant care station with at least one access point in a sealed position or obtaining, detecting, or otherwise receiving an ambient measurement. In some examples, the sealed measurement can be obtained as a predetermined value detected using one or more sensors of an infant care station when the access points are sealed or closed. The sensors can detect any suitable sealed measurement such as a pressure level within the microenvironment of the infant care station, a humidity level within the microenvironment of the infant care station, an oxygen level within the microenvironment of the infant care station, a temperature control loop value, or any combination thereof. The temperature control loop value can indicate any suitable measurement used to control a fan motor, a heater duty cycle, a radiant heater fan speed, or the like. The temperature control loop value can be obtained with any suitable control loop sensor that monitors the power consumption of heating components within an infant care station. In some examples, the temperature control loop value can indicate a fan speed, heater elements on or off times, an increased wattage for a radiant heater, and an increased wattage for a humidifier heater, among others. The temperature control loop value can represent when a heater of an infant care station is providing heat to a microenvironment. In some examples, the temperature control loop value is modified in response to detecting a temperature variation in the microenvironment. For example, an increase or a decrease of a temperature of the microenvironment can cause a heater of an infant care station to provide a modified amount of heat so that the temperature of the microenvironment is maintained within a predetermined temperature range.

In some examples, the method 400 can detect, determine, or otherwise obtain an ambient measurement instead of, or in addition to, obtaining a sealed measurement. The ambient measurement can be measured or obtained by an ambient sensor monitoring the environment proximate an infant care station as described in greater detail above in relation to FIG. 3. The ambient measurement can indicate a pressure level or humidity level, among others, of the environment surrounding an infant care station.

At block 404, the method 400 can include obtaining the environmental characteristic from one or more microenvironment sensors monitoring the microenvironment. The microenvironment sensors can include pressure sensors, humidity sensors, oxygen sensors, and the like. In some examples, the microenvironment sensors can be placed at any suitable location within the enclosure or cabin of an infant care station to monitor environmental characteristics such as pressure levels, oxygen levels, and humidity levels, among others. For example, pressure sensors, oxygen sensor, humidity sensors, and the like, can be placed proximate to porthole doors or canopies, among other access points. In some examples, one or more pressure sensors can be included within an infant care station to detect a set of pressure values from different locations within the microenvironment. The set of pressure values can enable a host device to determine an average pressure value or a difference in pressure values. The difference in pressure values can be used to calculate or compute a rate of change in the pressure values detected by each of the pressure sensors, which can indicate the pressure sensor that is closest to an unsealed or open access point. In some examples, multiple pressure sensors, oxygen sensors, humidity sensors, or other microenvironment sensors, can be used to determine an open or unsealed access point by detecting the microenvironment sensor that is monitoring the faster rate of change as compared to other microenvironment sensors in the infant care station.

The method 400 can also include obtaining sensor data values from different types of sensors monitoring the microenvironment of an infant care station. In some examples, the sensors can obtain sensor data directly from the microenvironment or indirectly by monitoring the operation of heaters and other components of the infant care station. For example, the sensors can indirectly determine a temperature change or temperature stability of the microenvironment of an infant care station by monitoring sensor data from control loop sensors that detect, determine, or otherwise obtain the temperature control loop values that represent the operation of radiant heaters, among other components, of the infant care station. In some examples, the sensors can detect sensor data indicating that a control loop for an infant care station is becoming more active, which can represent a perturbation of the microenvironment of the infant care station via the increased control loop activity.

At block 406, the method 400 can include determining a difference between the environmental characteristic and either the sealed measurement or the ambient measurement. As discussed above in relation to block 402, the sealed measurement can be obtained from the microenvironment of the infant care station with the access points in a sealed or closed position and the ambient measurement can be obtained from any suitable ambient sensor. The difference between either the environment characteristic and the sealed measurement or the environmental characteristic and the ambient measurement can represent a step change in pressure, oxygen level, humidity, and the like, within the microenvironment of an infant care station. The difference can indicate that one or more access points may have been unsealed or opened for a period of time. For example, the difference can indicate that a porthole door, a canopy, or any other suitable access point of an infant care station has been opened. In some examples, an open access point can enable warm air from the microenvironment to exit the infant care station into the surrounding environment. The difference can also indicate that the infant care station has transitioned from an open canopy position to a closed canopy position.

In some examples, the sensors can also include global positioning system (GPS) coordinates that map the location of the infant care station to a known altitude. The known altitude can be used when determining if the environmental characteristic exceeds a predetermined threshold. For example, the altitude can be used to determine an expected pressure of the environment surrounding the infant care station, an expected baseline pressure of the microenvironment in an unsealed or open position, or the like.

At block 408, the method 400 can include generating an alert indicating an access point sealing issue based on the difference exceeding a predetermined threshold. The access point sealing issue, as referred to herein, can indicate an unexpected open or unsealed access point or an unexpected, sealed access point. For example, the access point sealing issue can indicate an open porthole door or a closed canopy, among others. In some examples, the alert can indicate an amount of time any number of access points have been open, whether the amount of time an access point has been open exceeds a predetermined threshold, a pressure value, an oxygen value, a humidity value, a rate of change in a set of pressure values, oxygen values, or humidity values, or a delta value representing a change in pressure values, oxygen values, or humidity values within a predetermined period of time, among others. In some examples, the alert can indicate values from two or more different types of sensors have exceeded predetermined thresholds. For example, the alert can indicate a difference between a measured pressure value and a predetermined sealed pressure value for the infant care station has exceeded a first threshold and a difference between a measured oxygen level and a predetermined sealed oxygen level for the infant care station has exceeded a second threshold. In some examples, any number of types of sensors can detect different sensor values and the alert can indicate if any of the different sensors obtain sensor values that exceed one or more thresholds. For example, the sensor devices can include sensors that monitor the pressure, humidity, and oxygen level of the microenvironment in addition to any number of sensors that monitor the temperature control loop values for an infant care station.

In some examples, the alert can be based on the difference between the environmental characteristic and the sealed measurement combined with a difference between the environmental characteristic and an ambient measurement. The ambient measurement can be obtained from an ambient sensor located outside of the microenvironment as described in greater detail above in relation to FIG. 3. In some examples, the unsealed pressure of a microenvironment of an infant care station can be lower than the sealed pressure of the infant care station, and yet can be higher than the ambient pressure level around the infant care station. The method 400 can include, in some examples, determining if one or more access points are unsealed based on whether the pressure of a microenvironment is closer to a sealed measurement or an ambient measurement.

Still at block 408, in some examples, the alert can indicate a particular access point that is experiencing an access point sealing issue. For example, the method 400 can include determining the rate of change of pressure within a microenvironment. A slower rate of change can indicate one or more porthole doors that are unsealed. A faster rate of change of the pressure level can indicate an open or closed canopy in an infant care station. In some examples, the method 400 can include obtaining predetermined rates of change in pressure, or any other suitable environmental characteristic, corresponding to one or two unsealed porthole doors, an unsealed canopy, or any other access points. The method 400 can include generating an alert that indicates the specific access points that are likely unsealed based on the predetermined rates of change in pressure or changes in other environmental characteristics. For example, the method 400 can include determining if one porthole door is unsealed with a sealed canopy, two porthole doors are unsealed with a sealed canopy, two porthole doors are sealed with an unsealed canopy, or any combination thereof.

In some examples, the alert can also include the sensor data detected from one or more microenvironment sensors such that the alert can indicate the pressure sensor values, humidity values, oxygen level values, temperature control loop values, and the like. The sensor data from the alert can be displayed by a display device coupled to an infant care station or a remote device that received the alert from the infant care station.

The process flow diagram of method 400 of FIG. 4 is not intended to indicate that all of the operations of blocks 402-408 of the method 400 are to be included in every example. Additionally, the process flow diagram of method 400 of FIG. 2 describes a possible order of executing operations. However, it is to be understood that the operations of the method 400 can be implemented in various orders or sequences. In addition, in some examples, the method 400 can also include fewer or additional operations. For example, the method 400 can include determining when a canopy of an infant care station is transitioned from an open position to a closed position. In the open position, the canopy does not contact all four side walls so that the microenvironment is exposed to the surrounding environment. In the closed position, the canopy contacts all four side walls of the infant care station to seal the microenvironment from the surrounding environment. When the canopy is in a closed position, a radiant heater can be turned off. In some examples, the method 400 can determine that the canopy is in a closed position by monitoring the environmental characteristic to determine an increase in a pressure value of the microenvironment, a temperature control loop value indicating that the heater is still in operation, or the like. The method 400 can generate an alert in response to detecting the heater of the infant care station is still operating with the canopy in a closed position. For example, the method 400 can include generating an alert when a pressure value from a microenvironment falls below a predetermined threshold and turning off the power to a heater of the infant care station.

Additionally, in some examples, the method 400 can include detecting a rate of change of an environmental characteristic and determining that the rate of change is below a predetermined threshold, which can indicate an issue with one or more equipment access points. For example, a gradual loss of pressure below a threshold value can indicate a damaged seal around one or more hoses, cables, and the like, that are placed through access point holes in the walls of an infant care station. In some examples, the method 400 can include generating an alert that indicates a damaged equipment access point in response to detecting a change in an environmental characteristic that is below a predetermined threshold.

Figure 5:
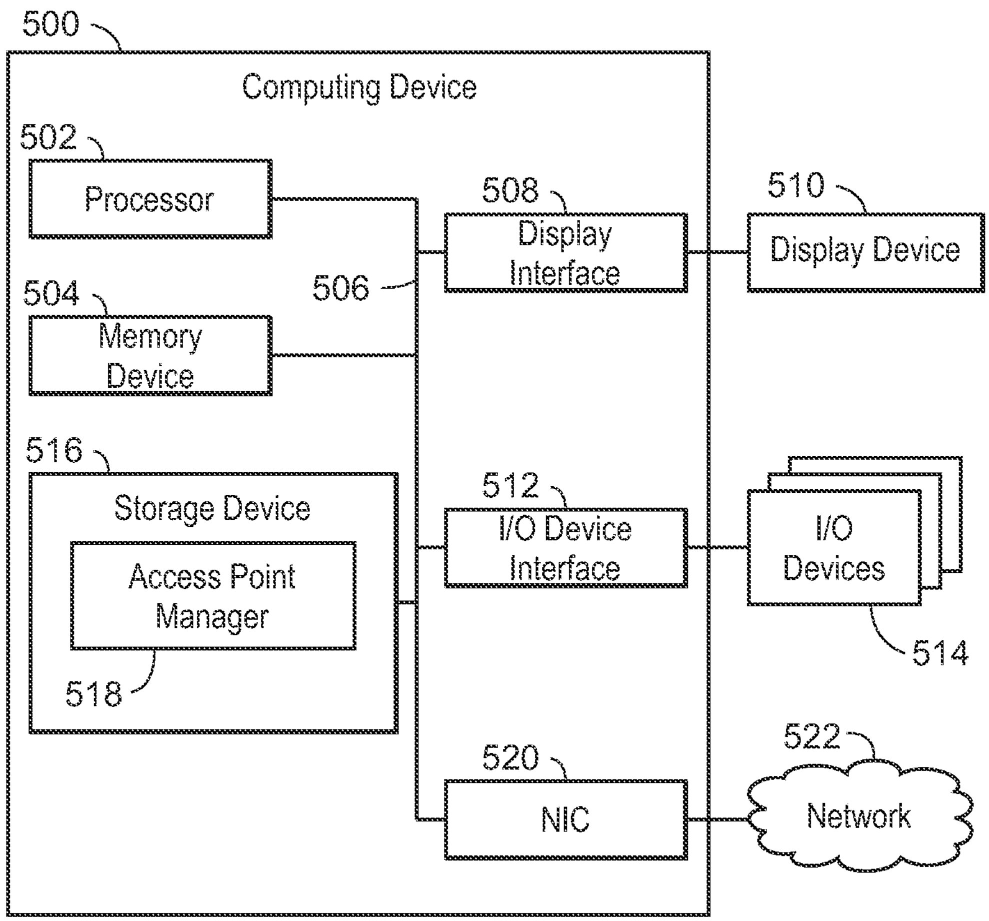
FIG. 5 is a block diagram of an example of a computing device that can detect an access point sealing issue of an infant care station.

FIG. 5 is a block diagram of an example of a computing device that can detect an access point sealing issue of an infant care station. The computing device 500 may be, for example, an infant care station device, such as an incubator, a warmer, or a device that provides features of both an incubator and a warmer, a laptop computer, a desktop computer, a tablet computer, or a mobile phone, among others. The computing device 500 may include a processor 502 that is adapted to execute stored instructions, as well as a memory device 504 that stores instructions that are executable by the processor 502. The processor 502 can be a single core processor, a multi-core processor, a computing cluster, or any number of other configurations. The memory device 504 can include random access memory, read only memory, flash memory, or any other suitable memory systems. The instructions that are executed by the processor 502 may be used to implement a method that can detect an open or unsealed access point of an infant care station, as described in greater detail above in relation to FIG. 4.

The processor 502 may also be linked through the system interconnect 506 (e.g., PCI, PCI-Express, NuBus, etc.) to a display interface 508 adapted to connect the computing device 500 to a display device 510. The display device 510 may include a display screen that is a built-in component of the computing device 500. The display device 510 may also include a computer monitor, television, or projector, among others, that is externally connected to the computing device 500. The display device 510 can include light emitting diodes (LEDs), and micro-LEDs, among others.

The processor 502 may be connected through a system interconnect 506 to an input/output (I/O) device interface 512 adapted to connect the computing device 500 to one or more I/O devices 514. The I/O devices 514 may include, for example, a keyboard and a pointing device, wherein the pointing device may include a touchpad or a touchscreen, among others. The I/O devices 514 may be built-in components of the computing device 500, or may be devices that are externally connected to the computing device 500.

In some embodiments, the processor 502 may also be linked through the system interconnect 506 to a storage device 516 that can include a hard drive, an optical drive, a USB flash drive, an array of drives, or any combinations thereof. In some embodiments, the storage device 516 can include any suitable applications. In some embodiments, the storage device 516 can include an access point manager 518. In some embodiments, the access point manager 518 can obtain a sealed measurement for an infant care station with at least one access point in a sealed position, obtain the environmental characteristic from one or more sensors, and determine a difference between the environmental characteristic and the sealed measurement. The access point manager 518 can also generate an alert indicating an access point sealing issue based on the difference. In some examples, the alert can also indicate that maintenance is to be scheduled for the access point and provide the alert using any suitable user interface or display device. For example, the alert can indicate that a latch or a gasket of a porthole may be malfunctioning, which prevents a porthole door from sealing. The alert can also indicate that a heater is not turning off when an infant care station transitions from a warmer with an open canopy to an incubator with a closed canopy. In some examples, the access point manager 518 can be stored in storage 516 or within memory device 504 accessible by the processor 502, among others.

The access point manager 518 can also obtain an ambient measurement from one or more ambient sensors for an environment proximate to an infant care station, obtain an environmental characteristic from one or more microenvironment sensors proximate to at least one access point of the infant care station, determine a difference between the environmental characteristic and the ambient measurement exceeds a predetermined threshold, and generate an alert indicating an access point sealing issue in the infant care station based on the difference exceeding the predetermined threshold. In some examples, the alert can be based on the difference between the environmental characteristic and the ambient measurement, based on the difference between the environment characteristic and a sealed measurement, or a combination thereof. In some examples, the access point manager 518 can generate a first alert in response to detecting a difference between a sealed measurement and an environmental characteristic. The access point manager 518 can also generate a second alert in response to detecting a difference between the ambient measurement and the environmental characteristic that exceeds an ambient threshold. The ambient threshold can indicate a maximum difference between the ambient measurement and the environmental characteristic before an alert is generated.

In some examples, the display device 510 can provide a user interface that indicates data from the alert such as sensor data from the microenvironment sensors, and the like. The display device 510 can also provide a visual representation of an infant care station, wherein the visual representation indicates which of the access points of the infant care station are in an unexpected sealed or unsealed position. For example, the display device 510 can provide a visual representation indicating an open porthole door, a closed canopy with a heater still generating heat for the microenvironment, or the like.

In some examples, the access point manager 518 can obtain proximity sensor data from one or more cameras, proximity sensors, and the like. The access point manager 518 can prevent generating or providing an alert if a user is detected in the proximity sensor data within a predetermined distance from an infant care station. For example, the access point manager 518 can obtain, detect, or otherwise receive proximity sensor data that indicates the presence of a user near an infant care station. In some examples, if the access point manager 518 detects an unsealed or open access point while a user is proximate to the infant care station, the access point manager 518 can prevent displaying or otherwise providing an alert. In some examples, the access point manager 518 can delay providing an alert for a predetermined period of time or delay providing an alert until a user is no longer in proximate to the infant care station.

In some examples, a network interface controller (also referred to herein as a NIC) 520 may be adapted to connect the computing device 500 through the system interconnect 506 to a network 522. The network 522 may be a cellular network, a radio network, a wide area network (WAN), a local area network (LAN), or the Internet, among others. The network 522 can enable data, such as alerts, among other data, to be transmitted from the computing device 500 to remote computing devices, remote display devices, remote user interfaces, and the like.

It is to be understood that the block diagram of FIG. 5 is not intended to indicate that the computing device 500 is to include all of the components shown in FIG. 5. Rather, the computing device 500 can include fewer or additional components not illustrated in FIG. 5 (e.g., additional memory components, embedded controllers, additional modules, additional network interfaces, etc.). Furthermore, any of the functionalities of the access point manager 518 may be partially, or entirely, implemented in hardware and/or in the processor 502. For example, the functionality may be implemented with an application specific integrated circuit, logic implemented in an embedded controller, or in logic implemented in the processor 502, among others. In some embodiments, the functionalities of the access point manager 518 can be implemented with logic, wherein the logic, as referred to herein, can include any suitable hardware (e.g., a processor, among others), software (e.g., an application, among others), firmware, or any suitable combination of hardware, software, and firmware.

Figure 6:
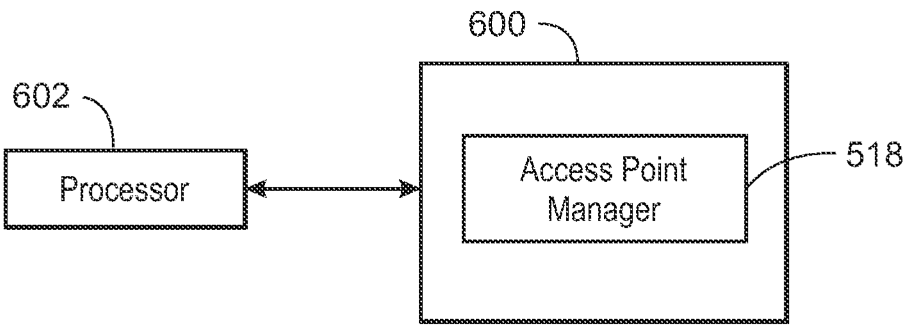
FIG. 6 depicts a non-transitory machine-executable medium with instructions that can detect an access point sealing issue in an infant care station.

FIG. 6 depicts a non-transitory machine-executable medium with instructions that can detect an access point sealing issue in an infant care station. The non-transitory, machine-readable medium 600 can cause a processor 602 to implement the functionalities of method 400. For example, a processor of an infant care station, a host device, a computing device (such as processor(s) 502 of computing device 500 of FIG. 5), or any other suitable device, can access the non-transitory, machine-readable media 600.

In some examples, the non-transitory, machine-readable medium 600 can include instructions to execute an access point manager 518. For example, the non-transitory, machine-readable medium 600 can include instructions that cause the processor 602 to obtain a sealed measurement for an infant care station with at least one access point in a sealed position, obtain the environmental characteristic from one or more sensors, and determine a difference between the environmental characteristic and the sealed measurement. The non-transitory, machine-readable medium 600 can also include instructions that cause the processor 602 generate an alert indicating an access point sealing issue based on the difference. In some examples, the non-transitory, machine-readable medium 600 can include instructions to implement any combination of the techniques of the method 400 described above.

For example, the machine-readable medium 600 can also include instructions to obtain an ambient measurement from one or more ambient sensors for an environment proximate to an infant care station, obtain an environmental characteristic from one or more microenvironment sensors proximate to at least one access point of the infant care station, determine a difference between the environmental characteristic and the ambient measurement exceeds a predetermined threshold, and generate an alert indicating an access point sealing issue in the infant care station based on the difference exceeding the predetermined threshold.

Figure 7:
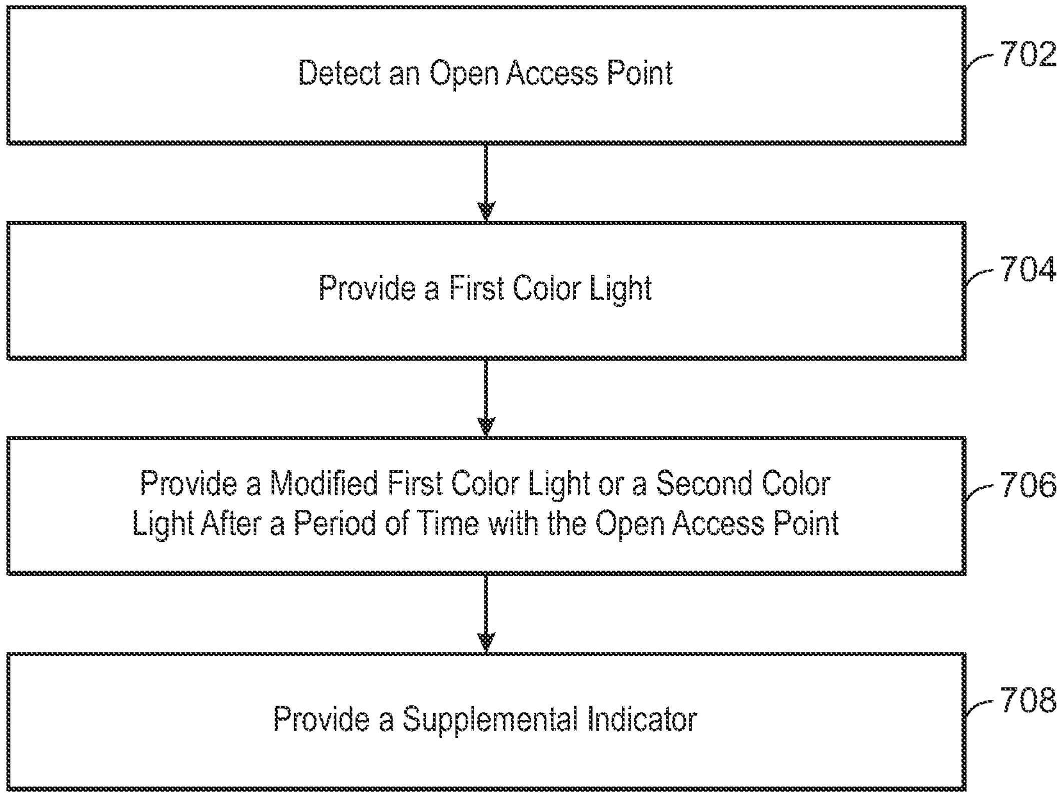
FIG. 7 depicts a process flow diagram of an example method for providing an open access point indicator in an infant care station.

FIG. 7 depicts a process flow diagram of an example method for providing an open access point indicator in an infant care station. The method 700 can be implemented with any suitable infant care station, such as the incubator 100 of FIG. 1, the infant care station 300 of FIG. 3, the infant care station 800 of FIG. 8, the infant care station 900A of FIG. 9A, the infant care station 900B of FIG. 9B, the infant care station 1000 of FIG. 10, or the computing device 1100 of FIG. 11, among others.

At block 702, the method can include detecting that at least one access point is open. In some examples, the method can include detecting a change in an environmental characteristic from a microenvironment of the infant care station. The environmental characteristic can include a temperature of the microenvironment, a humidity level of the microenvironment, or an oxygen level of the microenvironment. In some examples, as described above in relation to FIG. 4, the environmental characteristic can be obtained, received, or otherwise determined based on sensor data from sensors monitoring the microenvironment of the infant care station. The sensors can be placed proximate or adjacent to one or more access points of an infant care station or at any other suitable location in the infant care station.

In some examples, the method can include detecting an open access point based on a change in environmental characteristics between an ambient air sensor value obtained from outside the infant care station and a sensor value obtained within the microenvironment of the infant care station. The method can also include detecting an open access point based on a difference or a change in environmental characteristics between an initial sensor value and a real-time sensor value. For example, the initial sensor value can indicate environmental characteristics when access points of an infant care station are in a closed position and a comparison of real-time values to the initial sensor value can indicate if an access point is open in the infant care station.

At block 704, the method can include providing, using the lighting system, a first color light in response to the detecting that the at least one access point is open. The first color light can be an indicator that an access point is open or unsealed for an amount of time that exceeds a predetermined threshold. In some examples, the lighting system is proximate or adjacent to the at least one access point that is open. The lighting system can include one or more lights, a light bar, or the like. In some examples, the first color light can indicate an open access point or any other suitable environmental characteristics for the infant care station. For example, the first color light can indicate whether a humidity level, temperature, oxygen level, or the like, has exceeded a set of high and/or low threshold values.

At block 706, the method can include providing the first color light with a modified brightness or provide a second color light with the lighting system after a predetermined period of time elapses with the at least one access point being open. For example, the method can include modifying or adjusting the brightness, hue, lightness, chroma, colorfulness, or saturation, among others, of the first color light as an indicator for an environmental characteristic that changes over time or as an amount of time that an environmental characteristic exceeds a threshold increases. For example, a first color light in a light system of an infant care station can be modified to provide a color with more brightness as the amount of time an access point is open increases or the amount of time an environmental characteristic of an infant care station exceeds a threshold value. In some examples, the lighting system can provide a first color light after an access point, such as a porthole door, canopy, or the like, is left in an open or unsealed position for 10 seconds, 30 seconds, 1 minute, 5 minutes, or any other suitable period of time. The lighting system can provide a second color light in response to the access point remaining in an open or unsealed position for 30 seconds, 1 minute, 2 minutes, or any other suitable period of time following the first color light being provided.

In some examples, the method can include providing a second color light with the same light that provides the first color of the lighting system or using a second light of the lighting system. For example, the color provided by a first light of the lighting system can transition or change to a second color after a predetermined period of time with an open access point. In some examples, the lighting system can include two or more lights and the second light can provide a color indicator after a period of time with an open access point. In some examples, the first color light and the second color light can be configured by a user to represent different environmental characteristics and/or an open access point. For example, the first color light and the second color light can be configurable such that any suitable color can indicate a particular environmental characteristic or an open access point.

At block 708, the method can include providing a supplemental indicator that includes a third color, an audible alert, a modified illumination of the lighting system of the infant care station, or the like. The supplemental indicator, as referred to herein, can represent any additional information regarding the environmental characteristics of the microenvironment of an infant care station, information related to an open or unsealed access point, or the like. For example, the method can also include providing a third color with the lighting system. The third color can represent the change in the environmental characteristic, an open access point, or the like. For example, a first light, a second light, or a combination thereof can provide color indicators that an access point is open in an infant care station. The third color can simultaneously indicate a change in environmental characteristics of the infant care station. For example, the third color can indicate a change in a temperature, humidity level, oxygen level, or the like of the infant care station.

In some examples, the method can include changing a portion of the lighting system that is illuminated based on the predetermined period of time in which the at least one access point is open or unsealed. For example, a number of lights or the area of the lighting system can provide more illumination as the time that an access point is open increases. In some examples, the method can include providing an audible alarm after the lighting system has provided the second color for a second period of time. The audible alarm can be provided by the infant care station or a remote system electronically coupled to the infant care station using any suitable wired or wireless protocol.

Still at block 708, in some examples, the lighting system can be located along an edge of a porthole door, and the method can include illuminating a first portion of the lighting system in response to the detecting that the at least one access point is open. The method can also include illuminating a second portion of the lighting system in response to the predetermined period of time elapsing with the at least one access point being open.

In some examples, the method can include obtaining lighting system data representing the first color, the second color, and a time that the access point is open, and transmitting the lighting system data to a remote device. For example, the lighting system data can be transmitted using any suitable wired or wireless protocol to a remote device. The remote device can display the lighting system data representing an amount of time each access point has been opened, the change in environmental characteristics, or the like.

In some examples, the method can include simultaneously providing two or more different color lights with the lighting system in response to detecting that at least one access point is open and detecting a reduction in a humidity level of a microenvironment of the infant care station or a reduction in a temperature of the microenvironment of the infant care station. For example, the method can include displaying a first color, such as red, blue, green, or the like, in response to detecting an open access point. The method can also include displaying a second color, third color, or any number of colors, wherein each color represents one or more environmental characteristics. For example, the second color can represent a change in a humidity level that exceeds a predetermined threshold, a third color can represent a change in a temperature that exceeds a predetermined threshold, a fourth color can represent a change in an oxygen level of the microenvironment that exceeds a predetermined threshold, and the like. In some examples, a second light or a third light, among others, can display a color that represents two or more environmental characteristics in a combined manner. For example, a particular color can be assigned to a combination of environmental characteristics to represent a change in humidity and a change in temperature that both exceed threshold values, a change in temperature and oxygen levels that both exceed threshold values, or any other suitable combination of environmental characteristics.

The process flow diagram of method 700 of FIG. 7 is not intended to indicate that all of the operations of blocks 702-708 of the method 700 are to be included in every example. Additionally, the process flow diagram of method 700 of FIG. 7 describes a possible order of executing operations. However, it is to be understood that the operations of the method 700 can be implemented in various orders or sequences. In addition, in some examples, the method 700 can also include fewer or additional operations. For example, the method can also include automatically initiating an air boost component in the infant care station in response to the detecting that at least one access point is open. The air boost component is described in greater detail below in relation to FIG. 10. In some examples, the method 700 can include detecting an open access point when an infant care station is in an open state or a closed state, or when any number of access points are open. An open state, as referred to herein, can include an infant care station with at least one open access point. A closed state, as referred to herein, can include an infant care station with each of the access points in a closed or sealed position.

Figure 8:
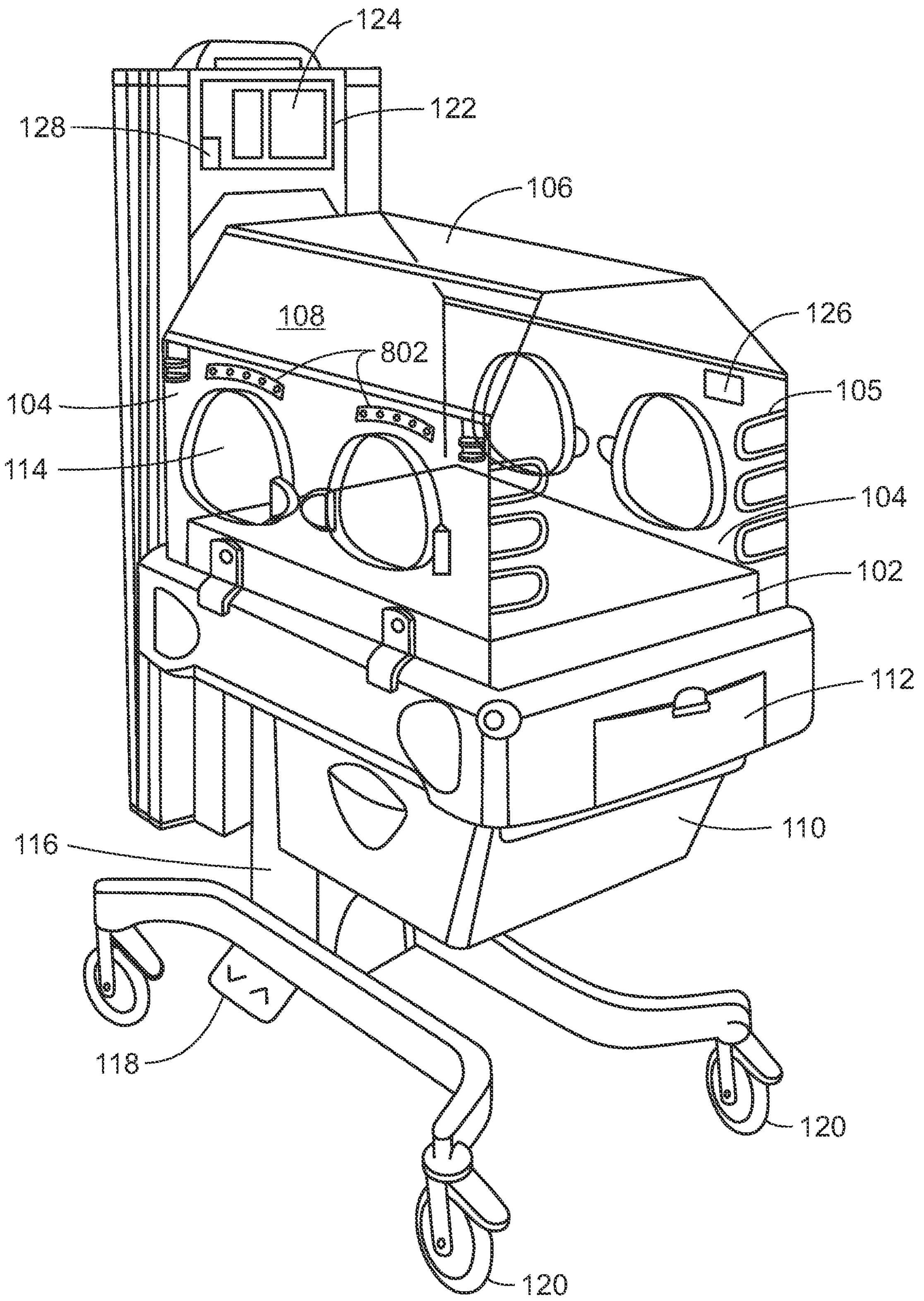
FIG. 8 is an example block diagram of an infant care station with a lighting system located adjacent to an access point.

FIG. 8 is an example block diagram of an infant care station with a lighting system located adjacent to an access point. In some examples, the infant care station 800 can include the various components and features of the incubator 100 of FIG. 1. Additionally, the infant care station 800 can include a lighting system, such as a light bar 802. The one or more light bars 802 can be coupled to or integrated within an infant care station 800. The light bars 802 can be curved along the perimeter of an access point, in a straight series of lights proximate or adjacent to the access point, or the like. In the example of FIG. 8, the light bars 802 are curved along the perimeter of portholes 114 in the walls 104 of infant care station 800.

The light bars 802 can provide any number of lights as time progresses with an environmental characteristic change driving an alert. For example, the light bars 802 can display a first light color or first light intensity for a portion of the light bars 802 in response to a change in environmental characteristics for an infant care station 800. The light bars 802 can display a second light color or second light intensity for a larger portion of the light bars 802 as time progresses with the change in the environmental characteristic. For example, if the change in the environmental characteristic corresponds to a change in the temperature of the infant care station, the light bar 802 can progressively display more lights or illuminate a larger portion of the light bar 802 as time progresses without the temperature of the infant care station 800 returning to an expected state or an expected temperature.

In some examples, each access point of an infant care station 800 can have a light bar adjacent to the access points 105, 106, and 114. Each light bar 802 can be individually triggered to provide an alert by a change in environmental characteristics proximate to the access point near the light bar 802. Alternatively, the light bars 802 can be interconnected and the light bars 802 can display a shared alert proximate to any number of access points 105, 106, and 114 in response to a change in environmental characteristics.

Figure 9A:
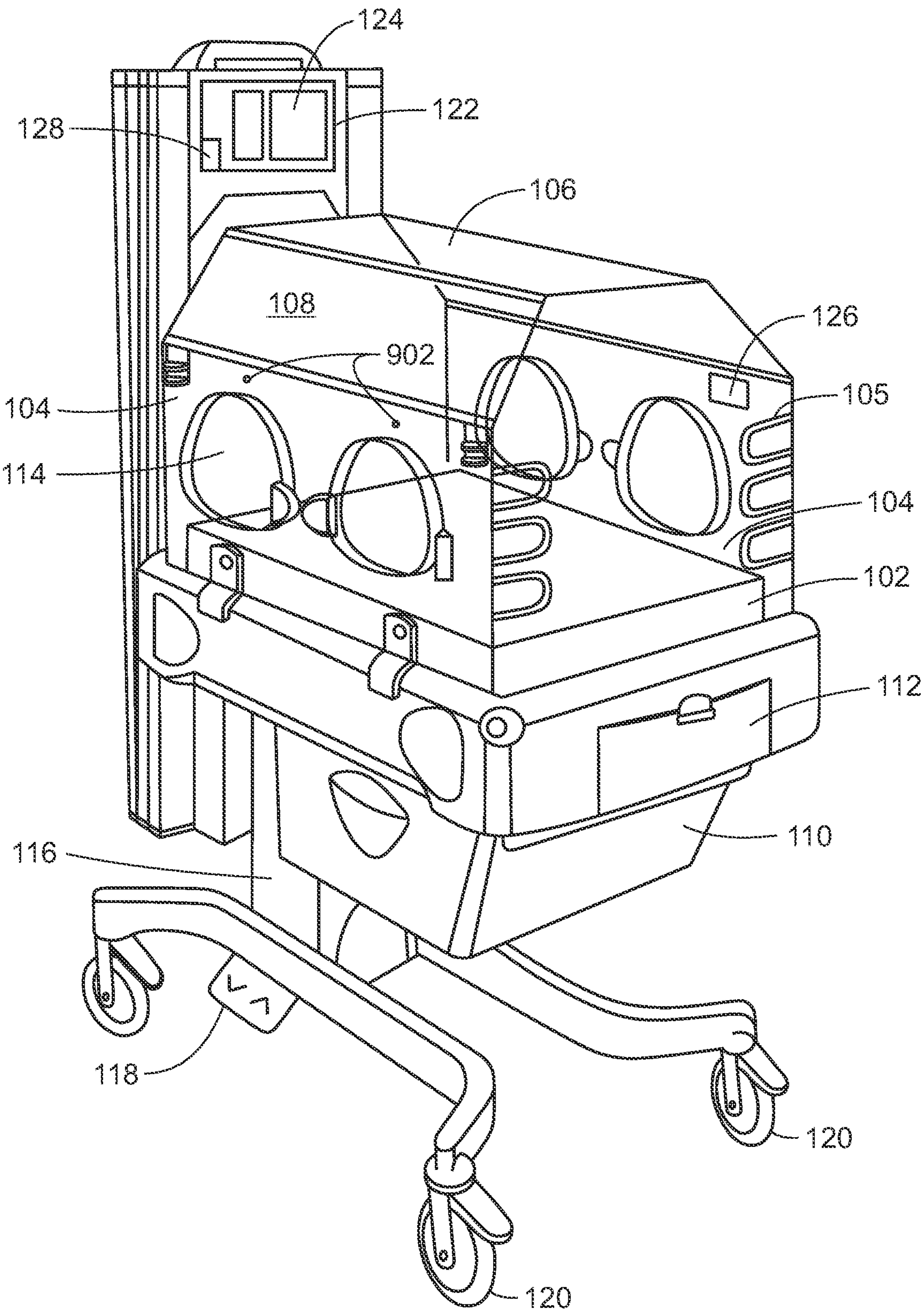
FIGS. 9A and 9B are example block diagrams of an infant care station with a lighting system located adjacent to an access point.
Figure 9B:
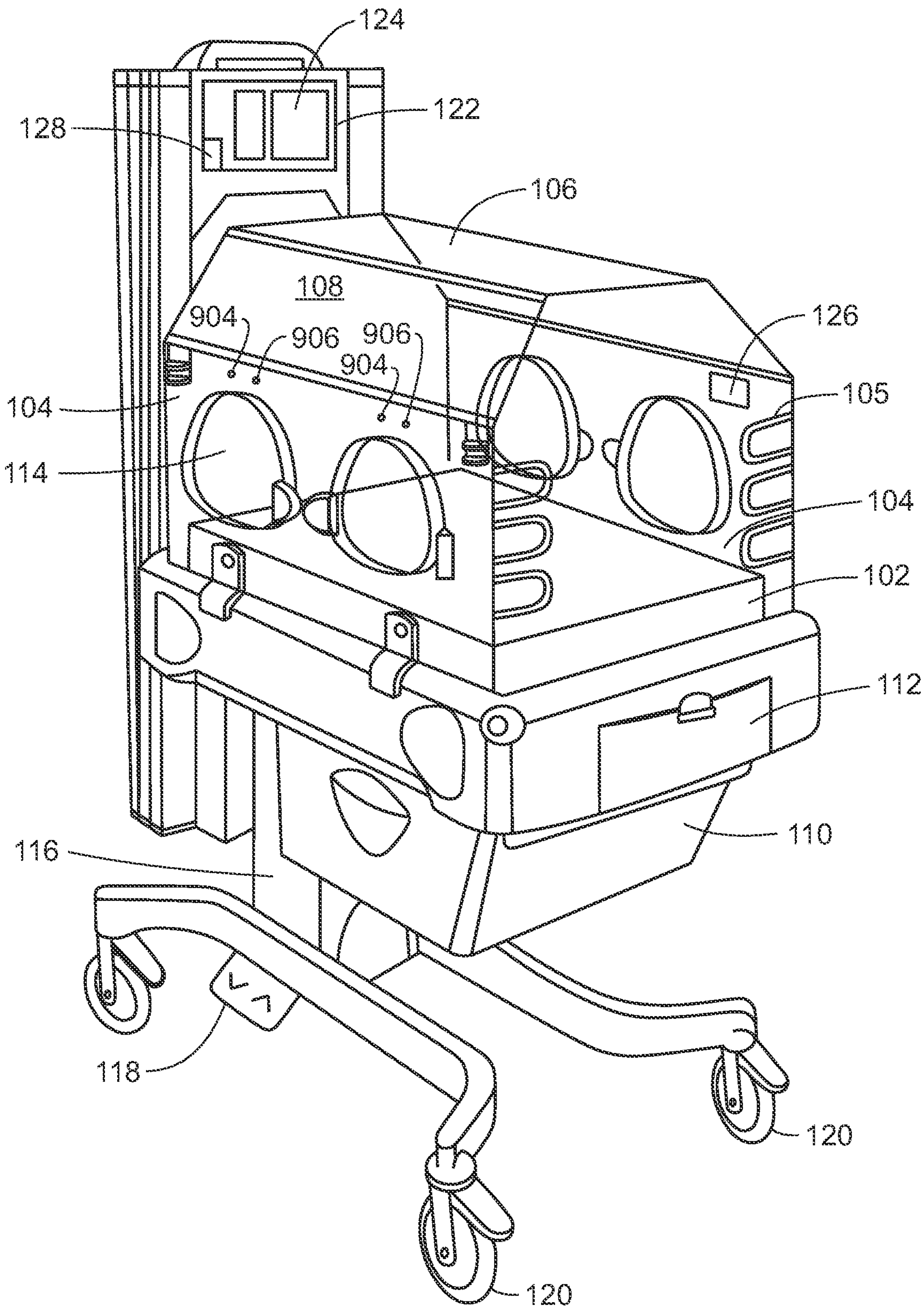

FIGS. 9A and 9B are example block diagrams of an infant care station with a lighting system located adjacent to an access point. In some examples, such as FIG. 9A, the lighting system can include a single light 902 that provides one or more colors. For example, the light 902 can provide a first color in response to detecting an open access point or a change in environmental characteristics of an infant care station 900A. The light 902 can provide a second color after a period of time in which the access point is still open, or the environmental characteristics are still outside of a threshold range. In some examples, as discussed above in relation to FIG. 7, the light 902 can change brightness or any other setting to indicate that an access point remains open, or an alert is still available regarding environmental characteristics.

In FIG. 9B, the lighting system of infant care station 900B can include two lights 904 and 906. The first light 904 can operate similarly to FIG. 9A by indicating an open access point 105, 106, or 114, or a change in environmental characteristics of the infant care station 900B. In some examples, the second light 906 of the lighting system can provide a same color as the first light 904 or a second color in response to a period of time elapsing without the access point 105, 106, or 114 being closed or the environmental characteristics changing to be within a predetermined threshold range. The second light 906 can, in some examples, alternatively provide a representation of the environmental characteristics as the first light 904 provides a representation of the access point 105, 106, or 114 being open. For example, the first light 904 can provide a first color in response to detecting an open access point 105, 106, or 114 and the second light 906 can provide a second color in response to detecting one or more environmental characteristics that are outside of a predetermined range.

In some examples, the lighting system of FIG. 9B can include more than two lights. The lights 904 and 906 of infant care station 900B can also be included in any suitable arrangement or orientation. For example, the lights 904 and 906 can be included at the top, bottom, sides, or any other suitable location adjacent to access points 105, 106, or 114, among others.

Figure 10:
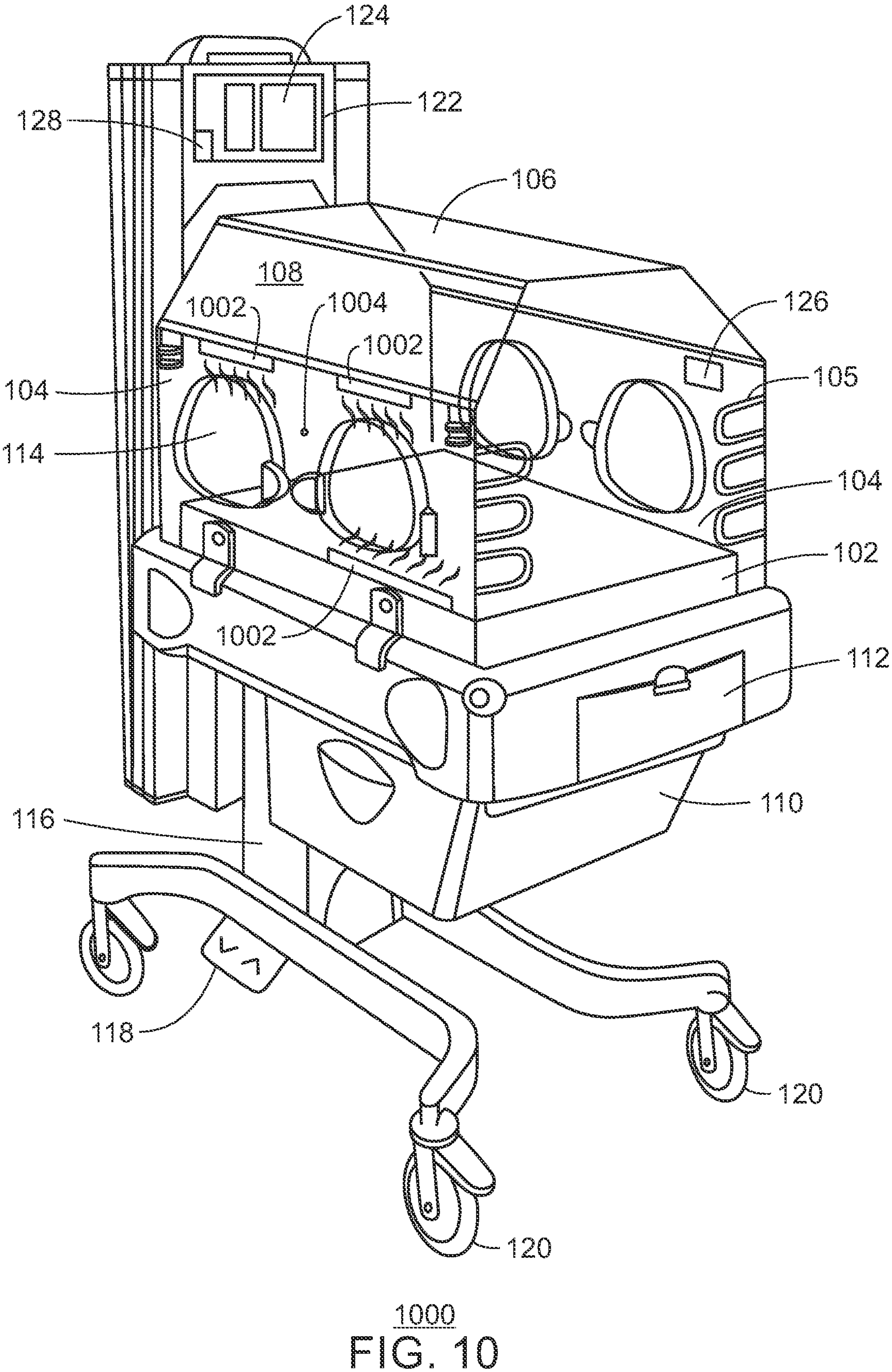
FIG. 10 is an example infant care station with an air boost component.

FIG. 10 is an example of an infant care station with an air boost component. In some examples, the infant care station can 1000 include an air boost component 1002 located along or proximate to one or more access points 105, 106, or 114. The air boost component 1002 can also be included under a mattress of an infant care station 1000, or at any other suitable location.

In some examples, the air boost component 1002 can project or extrude high pressure air to prevent the microenvironment of the infant care station 1000 from interacting with ambient air located outside of the infant care station 1000. For example, the air boost component 1002 can include a fan or any other suitable component of an infant care station 1000 that can increase the speed at which air is circulated along one or more walls and a canopy of an infant care station 1000. The air boost component 1002 can include, in some examples, a speed control for one or more fans of an infant care station 1000 that causes the one or more fans to increase speed in order to circulate more air within the microenvironment of the infant care station 1000. For example, the air boost component 1002 can cause a fan of an infant care station 1000 to rotate at a higher rate of revolutions per minute in response to detecting an open access point.

The air boost component 1002 can be enabled in response to detecting an open access point 105, 106, or 114 in the infant care station 1000. For example, the infant care station 1000 can detect an open access point 105, 106, or 114 and enable or engage the air boost component 1002 to prevent a change in the environmental characteristics of the infant care station 1000. In some examples, the air boost component 1002 can be enabled or engaged as a lighting system 1004 is activated to indicate an open access point 105, 106, or 114. The lighting system 1004 can have one or more lights to indicate that the air boost component 1002 has been activated. In addition, the infant care station 1000 can have one or more display devices, such as graphical display 122, that indicate when the air boost component 1002 is engaged or activated.

Figure 11:
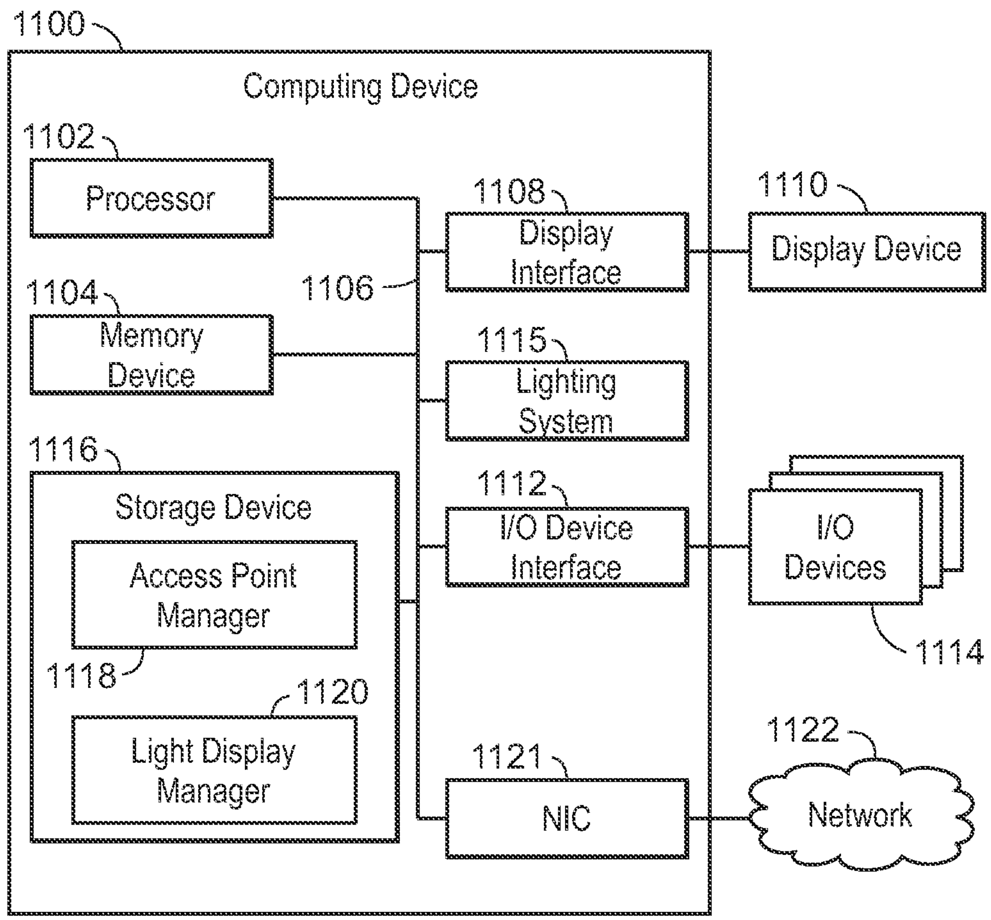
FIG. 11 is an example computing device that can provide an open access point indicator for an infant care station.

FIG. 11 is an example computing device that can provide an open access point indicator for an infant care station. The computing device 1100 may be, for example, an infant care station device, such as an incubator, a warmer, or a device that provides features of both an incubator and a warmer, a laptop computer, a desktop computer, a tablet computer, or a mobile phone, among others. The computing device 1100 may include a processor 1102 that is adapted to execute stored instructions, as well as a memory device 1104 that stores instructions that are executable by the processor 1102. The processor 1102 can be a single core processor, a multi-core processor, a computing cluster, or any number of other configurations. The memory device 1104 can include random access memory, read only memory, flash memory, or any other suitable memory systems. The instructions that are executed by the processor 1102 may be used to implement a method that can detect an open or unsealed access point of an infant care station and illuminate a lighting system of the infant care station, as described in greater detail above in relation to FIG. 7.

The processor 1102 may also be linked through the system interconnect 1106 (e.g., PCI, PCI-Express, NuBus, etc.) to a display interface 1108 adapted to connect the computing device 1100 to a display device 1110. The display device 1110 may include a display screen that is a built-in component of the computing device 1100. The display device 1110 may also include a computer monitor, television, or projector, among others, that is externally connected to the computing device 1100. The display device 1110 can include light emitting diodes (LEDs), and micro-LEDs, among others.

The processor 1102 may be connected through a system interconnect 1106 to an input/output (I/O) device interface 1112 adapted to connect the computing device 1100 to one or more I/O devices 1114. The I/O devices 1114 may include, for example, a keyboard and a pointing device, wherein the pointing device may include a touchpad or a touchscreen, among others. The I/O devices 1114 may be built-in components of the computing device 1100, or may be devices that are externally connected to the computing device 1100.

The processor 1102 can also be connected through a system interconnect 1106 to a lighting system 1115. In some examples, the lighting system 1115 can include any number of lights, such as light emitting diodes, among others. The lights of the lighting system 1115 can be arranged in any suitable configuration, such as a rectangle, square, circle, or the like, along an edge of an infant care station. For example, the lighting system 1115 can include lights that are arranged adjacent to or proximate to any number of access points such as porthole doors, canopies, and the like of an infant care station. In some examples, the lighting system 1115 can also include any number of components to illuminate one or more lights. The components can include power adapters, analog-to-digital converters, and the like.

In some embodiments, the processor 1102 may also be linked through the system interconnect 1106 to a storage device 1116 that can include a hard drive, an optical drive, a USB flash drive, an array of drives, or any combinations thereof. In some embodiments, the storage device 1116 can include any suitable applications. In some embodiments, the storage device 1116 can include an access point manager 1118 and a light display manager 1120. In some embodiments, the access point manager 1118 can detect that the at least one access point is open using any suitable technique, such as the method 400 of FIG. 4, among others. The light display manager 1120 can provide, using the lighting system 1115, a first color light in response to the detecting that the at least one access point is open. In some examples, the light display manager 1120 can also provide the first color light with a modified brightness or provide a second color light with the lighting system 1115 after a predetermined period of time elapses with at least one access point being open.

In some examples, the display device 1110 can provide a user interface that indicates data from the alert such as sensor data from the microenvironment sensors, and the like. The display device 1110 can also provide a visual representation of an infant care station, wherein the visual representation indicates which of the access points of the infant care station are in an unexpected sealed or unsealed position. For example, the display device 1110 can provide a visual representation indicating an open porthole door, a closed canopy with a heater still generating heat for the microenvironment, or the like. The display device 1110 can also provide a status of the lighting system 1115 of the computing device 1100. For example, the display device 1110 can indicate if one or more lights of the lighting system 1115 are illuminated and provide information, such as lighting system data, that explains the status of the one or more lights. The lighting system data, as referred to herein, can include data representing a first color of a lighting system, a second color of a lighting system, or any other number of colors provided by a lighting system along with a time that one or more access points are open and one or more environmental characteristics that exceed a predetermined range.

In some examples, a network interface controller (also referred to herein as a NIC) 1121 may be adapted to connect the computing device 1100 through the system interconnect 1106 to a network 1122. The network 1122 may be a cellular network, a radio network, a wide area network (WAN), a local area network (LAN), or the Internet, among others. The network 1122 can enable data, such as alerts, among other data, to be transmitted from the computing device 1100 to remote computing devices, remote display devices, remote user interfaces, and the like.

It is to be understood that the block diagram of FIG. 11 is not intended to indicate that the computing device 1100 is to include all of the components shown in FIG. 11. Rather, the computing device 1100 can include fewer or additional components not illustrated in FIG. 11 (e.g., additional memory components, embedded controllers, additional modules, additional network interfaces, etc.). Furthermore, any of the functionalities of the access point manager 1118 may be partially, or entirely, implemented in hardware and/or in the processor 1102. For example, the functionality may be implemented with an application specific integrated circuit, logic implemented in an embedded controller, or in logic implemented in the processor 1102, among others. In some embodiments, the functionalities of the access point manager 1118 and the light display manager 1120 can be implemented with logic, wherein the logic, as referred to herein, can include any suitable hardware (e.g., a processor, among others), software (e.g., an application, among others), firmware, or any suitable combination of hardware, software, and firmware.

Figure 12:
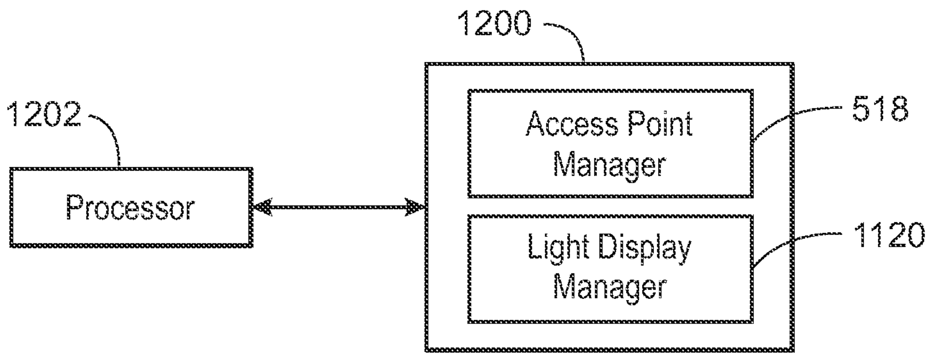
FIG. 12 depicts a non-transitory machine-executable medium with instructions that can provide open access point indicators for an infant care station.

FIG. 12 depicts a non-transitory machine-readable medium with instructions that can provide open access point indicators for an infant care station. The non-transitory, machine-readable medium 1200 can cause a processor 1202 to implement the functionalities of method 700. For example, a processor of an infant care station, a host device, a computing device (such as processor(s) 1102 of computing device 1100 of FIG. 11), or any other suitable device, can access the non-transitory, machine-readable media 1200.

In some examples, the non-transitory, machine-readable medium 1200 can include instructions to execute an access point manager 518 and a light display manager 1120. For example, the non-transitory, machine-readable medium 1200 can include instructions that cause the processor 1202 to detect an open access point. The non-transitory, machine-readable medium 1200 can also include instructions that cause the processor 1202 to provide, using the lighting system, a first color light in response to the detecting that the at least one access point is open and provide the first color light with a modified brightness or provide a second color light with the lighting system after a predetermined period of time elapses with the at least one access point being open. In some examples, the non-transitory, machine-readable medium 1200 can include instructions to implement any combination of the techniques of the method 700 described above.

Figure 13:
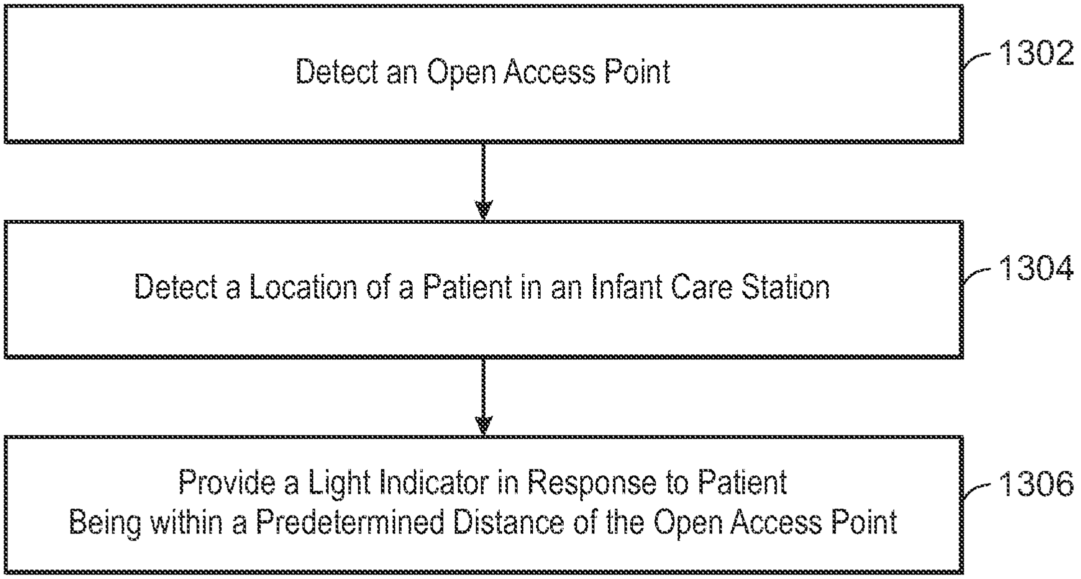
FIG. 13 is an example process flow diagram of a method for providing an indicator in response to detecting movement of a patient in an infant care station.

FIG. 13 is an example process flow diagram of a method for providing an indicator in response to detecting movement of a patient in an infant care station. The method 1300 can be implemented with any suitable device, such as the incubator 100 of FIG. 1, the infant care station 300 of FIG. 3, the infant care station 800 of FIG. 8, the infant care station 900A of FIG. 9A, the infant care station 900B of FIG. 9B, the infant care station 1000 of FIG. 10, or the computing device 1100 of FIG. 11, among others.

In some examples, the method 1300 can include, at block 1302, detecting an open access point as described above in greater detail in relation to block 702 of FIG. 7. For example, the method 1300 can include detecting an open access point based on any suitable sensor data obtained or received from sensors located in or adjacent to an infant care station.

The method 1300 can also include detecting, at block 1304, a location of a patient within an infant care station. In some examples, the location of the patient can be determined based on sensor data collected or obtained by accelerometers, radar sensors, light sensors, or the like. The sensors can be coupled to the patient, such as accelerometers coupled to any suitable portion of a patient. In some examples, the sensors can also reside in the infant care station. For example, any light sensors, radar sensors, or the like, can reside in the infant care station and can monitor a location of a patient within an infant care station.

The method 1300 can also include providing, at block 1306, a light indicator in response to detecting the location of the patient is within a threshold distance of the open access point. For example, the method 1300 can include providing any suitable color light with a lighting system of an infant care station in response to a patient changing location to be within a predetermined threshold distance from an open or unsealed access point.

Figure 14:
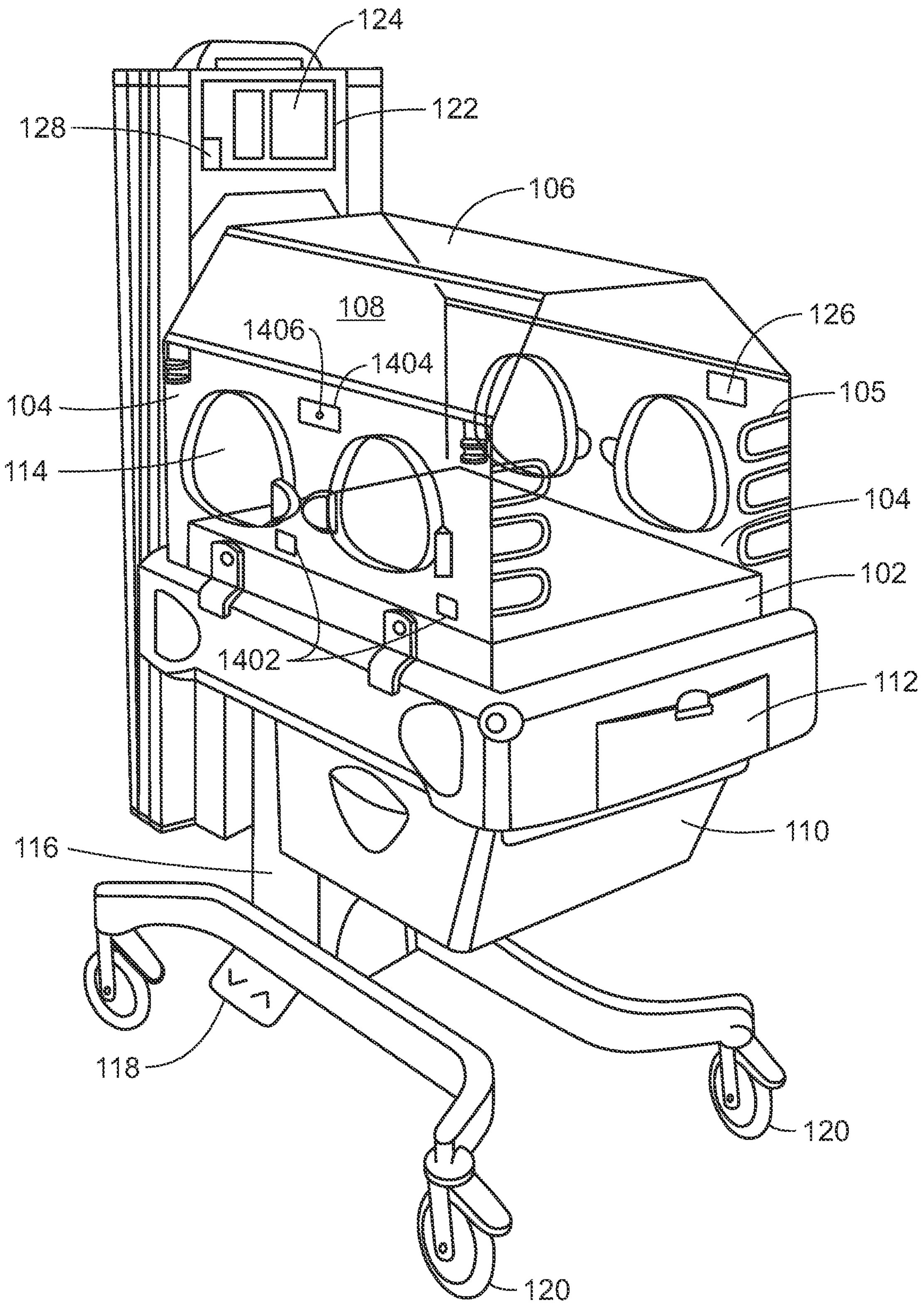
FIG. 14 is a block diagram of an example infant care station that can detect a location of a patient and provide an indicator with a lighting system.

FIG. 14 is a block diagram of an example infant care station that can detect a location of a patient and provide an indicator with a lighting system. In some examples, the infant care station can 1400 can include any number of sensors 1402 such as a radar sensor, a light sensor, or the like. In some examples, the sensors 1402 can be coupled or attached to the infant care station 1400 or coupled to or attached to a patient. The sensors 1402 can obtain sensor data about the location of a patient and determine if the patient is within a predetermined distance from an open access point.

In some examples, the infant care station 1400 can include a lighting system 1404 that can provide an indicator that a patient is within a threshold distance from an open access point. For example, the lighting system 1404 can have one or more lights 1406 that provide a color indicator representing a presence of a patient within a predetermined distance from an open access point. In some examples, the lighting system 1404 can turn off the one or more lights 1406 in response to detecting the patient is no longer within a predetermined distance from an open access point.

EXAMPLES

In one example, an infant care station can include a lighting system, at least one access point, and a processor that can detect that the at least one access point is open. The processor can also provide, using the lighting system, a first color light in response to the detecting that the at least one access point is open, and provide the first color light with a modified brightness or provide a second color light with the lighting system after a predetermined period of time elapses with the at least one access point being open.

Alternatively, or in addition, the processor can detect a change in an environmental characteristic from a microenvironment of the infant care station, wherein the environmental characteristic comprises a temperature of the microenvironment, a humidity level of the microenvironment, or an oxygen level of the microenvironment. Alternatively, or in addition, the processor can provide a third color with the lighting system, wherein the third color represents the change in the environmental characteristic. Alternatively, or in addition, the processor can change a portion of the lighting system that is illuminated based on the predetermined period of time in which the at least one access point is open.

Alternatively, or in addition, processor can provide an audible alarm after the lighting system has provided the second color for a second period of time. Alternatively, or in addition, the lighting system can be proximate to the at least one access point that is open. Alternatively, or in addition, the processor can automatically initiate an air boost component in the infant care station in response to the detecting that the at least one access point is open. Alternatively, or in addition, the lighting system can be located along an edge of a porthole door, and the processor can illuminate a first portion of the lighting system in response to the detecting that the at least one access point is open and illuminate a second portion of the lighting system in response to the predetermined period of time elapsing with the at least one access point being open.

Alternatively, or in addition, the processor can obtain lighting system data representing the first color light, the second color light, and a time that the access point is open and transmit the lighting system data to a remote device. Alternatively, or in addition, the processor can simultaneously provide two or more different color lights with the lighting system in response to detecting that the at least one access point is open and detecting a reduction in a humidity level of a microenvironment of the infant care station or a reduction in a temperature of the microenvironment of the infant care station.

In another example, a method for illuminating an infant care station can include detecting that at least one access point is open using a sensor in the infant care station, providing, using a lighting system, a first color light in response to the detecting that the at least one access point is open, and providing the first color light with a modified brightness or provide a second color light with the lighting system after a predetermined period of time elapses with the at least one access point being open.

Alternatively, or in addition, the method can include detecting a change in an environmental characteristic from a microenvironment of the infant care station, wherein the environmental characteristic comprises a temperature of the microenvironment, a humidity level of the microenvironment, or an oxygen level of the microenvironment. Alternatively, or in addition, the method can include providing a third color with the lighting system, wherein the third color represents the change in the environmental characteristic. Alternatively, or in addition, the method can include changing a portion of the lighting system that is illuminated based on the predetermined period of time in which the at least one access point is open. Alternatively, or in addition, the method can include providing an audible alarm after the lighting system has provided the second color for a second period of time.

Alternatively, or in addition, the lighting system is proximate to the at least one access point that is open. Alternatively, or in addition, the method can include automatically initiating an air boost component in the infant care station in response to the detecting that the at least one access point is open. Alternatively, or in addition, the lighting system is located along an edge of a porthole door, and the method can include illuminating a first portion of the lighting system in response to the detecting that the at least one access point is open and illuminating a second portion of the lighting system in response to the predetermined period of time elapsing with the at least one access point being open. Alternatively, or in addition, the method can include obtaining lighting system data representing the first color light, the second color light, and a time that the access point is open and transmitting the lighting system data to a remote device.

In another example, a non-transitory machine-readable media can include a plurality of instructions that in response to execution by a processor, cause the processor to detect that the at least one access point is open. The plurality of instructions can also cause the processor to provide, using the lighting system, a first color light in response to the detecting that the at least one access point is open and provide the first color light with a modified brightness or provide a second color light with the lighting system after a predetermined period of time elapses with the at least one access point being open. In some examples, the plurality of instructions can cause the processor to obtain lighting system data representing the first color, the second color, and a time that the access point is open and transmit the lighting system data to a remote device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Embodiments of the present disclosure shown in the drawings and described above are example embodiments only and are not intended to limit the scope of the appended claims, including any equivalents as included within the scope of the claims. Various modifications are possible and will be readily apparent to the skilled person in the art. It is intended that any combination of non-mutually exclusive features described herein are within the scope of the present invention. That is, features of the described embodiments can be combined with any appropriate aspect described above and optional features of any one aspect can be combined with any other appropriate aspect. Similarly, features set forth in dependent claims can be combined with non-mutually exclusive features of other dependent claims, particularly where the dependent claims depend on the same independent claim. Single claim dependencies may have been used as practice in some jurisdictions require them, but this should not be taken to mean that the features in the dependent claims are mutually exclusive.

What is claimed is:

1. An infant care station comprising:

a lighting system located along an edge of a porthole door;

a sensor;

at least one access point; and a processor to:

detect that the at least one access point is open using the sensor;

provide, using the lighting system, a first color light in response to the detecting that the at least one access point is open;

provide the first color light with a modified brightness or provide a second color light with the lighting system after a predetermined period of time elapses with the at least one access point being open;

illuminate a first portion of the lighting system in response to the detecting that the at least one access point is open; and illuminate a second portion of the lighting system in response to the predetermined period of time elapsing with the at least one access point being open.

2. The infant care station of claim 1, wherein the processor is to detect a change in an environmental characteristic from a microenvironment of the infant care station using the sensor, wherein the environmental characteristic comprises a temperature of the microenvironment, a humidity level of the microenvironment, or an oxygen level of the microenvironment.

3. The infant care station of claim 1, wherein the processor is to change a portion of the lighting system that is illuminated based on the predetermined period of time in which the at least one access point is open.

4. The infant care station of claim 1, wherein the lighting system is proximate to the at least one access point that is open.

5. The infant care station of claim 1, wherein the processor is to automatically initiate an air boost component in the infant care station in response to the detecting that the at least one access point is open.

6. The infant care station of claim 2, wherein the processor is to simultaneously provide two or more different color lights with the lighting system in response to detecting that the at least one access point is open and detecting a reduction in the humidity level of the microenvironment of the infant care station or a reduction in the temperature of the microenvironment of the infant care station.

* * * * *